United States Patent
Hieb et al.

(10) Patent No.: US 8,882,708 B2
(45) Date of Patent: Nov. 11, 2014

(54) MATING MECHANISM FOR A PRESSURIZING UNIT AND CORRESPONDING SLEEVE IN A MEDICAL FLUID INJECTION DEVICE

(75) Inventors: Marty Hieb, St. Louis Park, MN (US); Khoi Le, Chanhassen, MN (US); Bill West, Eden Prairie, MN (US); Darryl Wrolson, Waconia, MN (US); Paul Pilosi, Minnetonka, MN (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 693 days.

(21) Appl. No.: 12/261,415

(22) Filed: Oct. 30, 2008

(65) Prior Publication Data

US 2010/0113923 A1 May 6, 2010

(51) Int. Cl.
*A61M 37/00* (2006.01)
*A61M 5/00* (2006.01)
*A61M 5/142* (2006.01)
*A61M 5/168* (2006.01)
*A61M 5/145* (2006.01)

(52) U.S. Cl.
CPC ........... *A61M 5/007* (2013.01); *A61M 5/14216* (2013.01); *A61M 5/16827* (2013.01); *A61M 2005/14553* (2013.01); *A61M 2205/6045* (2013.01)
USPC ....................................................... 604/131

(58) Field of Classification Search
USPC ............. 604/131, 152, 154, 155; 128/DIG. 1, 128/DIG. 12
See application file for complete search history.

(56) References Cited

U.S. PATENT DOCUMENTS

| 4,677,980 | A | * | 7/1987 | Reilly et al. ................... 600/432 |
| 5,300,031 | A | * | 4/1994 | Neer et al. ..................... 604/154 |
| 5,383,858 | A | * | 1/1995 | Reilly et al. ................... 604/152 |
| 5,520,653 | A | | 5/1996 | Reilly et al. |
| 5,573,515 | A | | 11/1996 | Wilson et al. |
| 5,865,805 | A | | 2/1999 | Ziemba |

(Continued)

FOREIGN PATENT DOCUMENTS

| EP | 0 170 009 A1 | 2/1986 |
| EP | 0170009 A1 | 2/1986 |

(Continued)

OTHER PUBLICATIONS

"ACIST CVi Contrast Delivery System User Manual", ACIST Medical Systems, Inc., Nov. 2005, (91 pages).

(Continued)

*Primary Examiner* — Nathan R Price
(74) *Attorney, Agent, or Firm* — Shumaker & Sieffert, P.A.

(57) ABSTRACT

In general, this disclosure relates to techniques for providing a mating mechanism between at least one pressurizing unit and at least one corresponding sleeve in a powered medical fluid injection device. An example powered medical fluid injection device includes a sleeve and an injector head coupled to the sleeve. The sleeve has a notch with a predefined shape and size. The sleeve is configured to receive a pressurizing unit (such as a syringe) having an external tab with a predefined shape and size that are substantially identical to the predefined shape and size of the notch in the sleeve, such that the tab mates with the notch when the sleeve receives the pressurizing unit. The injector head is configured to inject a quantity of a medical fluid from the pressurizing unit during operation.

11 Claims, 14 Drawing Sheets

(56) References Cited

U.S. PATENT DOCUMENTS

| | | |
|---|---|---|
| 5,882,343 A | 3/1999 | Wilson et al. |
| 6,656,157 B1 | 12/2003 | Duchon et al. |
| 6,752,789 B2 | 6/2004 | Duchon et al. |
| 6,929,619 B2 * | 8/2005 | Fago et al. ............... 604/67 |
| 7,101,352 B2 | 9/2006 | Duchon et al. |
| 7,169,135 B2 | 1/2007 | Duchon et al. |
| 7,182,751 B2 | 2/2007 | Nemoto et al. |
| 2001/0011163 A1 | 8/2001 | Nolan et al. |
| 2006/0079765 A1 * | 4/2006 | Neer et al. ............... 600/432 |
| 2006/0184124 A1 * | 8/2006 | Cowan et al. ............ 604/155 |

FOREIGN PATENT DOCUMENTS

| | | |
|---|---|---|
| EP | 1 570 874 A2 | 9/2005 |
| EP | 1570874 A2 | 9/2005 |
| JP | 2004-194877 A | 7/2004 |
| WO | WO 2005/102416 A1 | 11/2005 |
| WO | WO 2007/033103 A1 | 3/2007 |
| WO | WO 2007/062315 A3 | 5/2007 |

OTHER PUBLICATIONS

Annex to Form PCT/ISA/206 Communication Relating to the Results of the Partial International Search from counterpart application No. PCT/US2009/062390, mailed Mar. 11, 2010, (2 pages).

Reply to Written Opinion for international application No. PCT/US2009/062390, filed Nov. 30, 2010, 5 pp.

International Search Report and Written Opinion of international application No. PCT/US2009/062390, mailed Sep. 1, 2010, 18 pages.

International Preliminary Report on Patentability for counterpart international application No. PCT/US2009/062390, dated Feb. 22, 2011, 11 pp.

Australian Patent Examination Report No. 1 for corresponding Australian patent application No. 2009314382, dated Dec. 17, 2012, 2 pages.

First Office Action and English Translation thereof for corresponding Chinese patent application No. 200980144650.0, dated Dec. 24, 2012, 10 pages.

Office Action and English Translation thereof for corresponding Korean patent application No. 10-2011-7011089, dated Mar. 28, 2013, 6 pages.

Office Action from Korean Intellectual Property Office dated Sep. 26, 2012, for corresponding Korean application No. 10-2011-7011089 (office action and translation are provided), 6 pages.

Japanese Office Action, English language Office Action Summary and Examiner's Opinion for corresponding Japanese Application No. 2011-534717, dated Nov. 27, 2012, 5 pages.

* cited by examiner

MATING MECHANISM FOR A PRESSURIZING UNIT AND CORRESPONDING SLEEVE IN A MEDICAL FLUID INJECTION DEVICE

TECHNICAL FIELD

This disclosure generally relates to the use of pressurizing units, such as syringes, within powered medical fluid injection devices.

BACKGROUND

Medical fluid injection devices are typically used to inject medical fluid into a patient. These devices often include one or more reservoirs to hold the medical fluid, and one or more pressurizing units to inject the medical fluid into the patient. For example, a contrast media powered injection device may include a reservoir containing contrast media and a syringe that is used to inject the contrast media into the patient. The contrast media injection device may be used during certain medical procedures, such as an angiographic or computed tomography (CT) procedure.

Many medical fluid injection devices include one or more syringes to inject fluid. A syringe has a chamber for holding the fluid and a plunger that is moveable within the chamber. The fluid is typically drawn into the chamber from a fluid reservoir when the plunger is moved in a first direction. The fluid is then expelled from the chamber and into the patient, via a catheter, when the plunger is moved in a second, opposite direction. The fluid is delivered at a rate that may be determined by a speed of movement of the plunger.

Typically, a container or sleeve is used to hold a syringe in place within a medical fluid injection device. In certain cases, the sleeve may have a movable door on one end, such that an operator may open the door and insert a syringe into a front-end of the sleeve. Such a process may be referred to as "front loading". In other cases, the sleeve may be fixedly attached to, yet rotatable about, a rod that is coupled to the device. An operator may rotate the sleeve away from the device for syringe insertion. After the operator has rotated the sleeve away from the device, the operator may slide the syringe into the sleeve. Then, the operator may rotate the sleeve back towards the device and position it into place, such that it is ready for use. In medical fluid injection devices that utilize two syringes (i.e., a dual-syringe device), two syringe sleeves may be used.

SUMMARY

In general, this disclosure relates to techniques for providing a mating mechanism between at least one pressurizing unit, such as a syringe, and at least one corresponding sleeve in a powered medical fluid injection device. For example, a pressurizing unit may have a tab with a predefined shape and size, and a corresponding sleeve of the injection device may have a notch with a substantially similar shape and size. The tab and notch constitute mating members, such that an operator may insert the pressurizing unit into the corresponding sleeve. The mating mechanism may allow an operator to properly align or position the pressurizing unit within the sleeve during insertion.

This disclosure also relates to techniques for manipulating at least one sleeve of the injection device. For example, a sleeve of the device may include one or more connectors that attach the sleeve to the device. These connectors of the sleeve may be coupled with an elongated rod of the device, such that the sleeve may be freely rotated by the operator into different operating positions. For example, the operator may manipulate the sleeve to rotate it around the rod into an unloaded position to insert a pressurizing unit into the sleeve. The operator may then rotate the sleeve into a loaded position, such that the injection device may fill fluid into or inject fluid from the pressurizing unit. When the sleeve is in the unloaded position, it may be completely removed from the injection device, such as when the operator pulls on the sleeve to detach the sleeve's connectors from the device.

In one embodiment, a powered medical fluid injection device includes a sleeve and an injector head coupled to the sleeve. The sleeve has a notch with a predefined shape and size. The sleeve is configured to receive a pressurizing unit (such as a syringe) having an external tab with a predefined shape and size that are substantially identical to the predefined shape and size of the notch in the sleeve, such that the tab mates with the notch when the sleeve receives the pressurizing unit. The mating of the tab with the notch may help ensure a proper alignment or positioning of the pressurizing unit within the sleeve.

In one embodiment, a powered medical fluid injection device includes a rod, a sleeve, and an injector head coupled to the rod. The sleeve is configured to receive a pressurizing unit, and includes at least one connector that is both rotatably and removably coupled to the rod. The injector head is configured to inject a quantity of a medical fluid from the pressurizing unit during operation. The sleeve becomes completely detached from the injection device when the at least one connector is removed from the rod by an operator upon completion of the injection of the quantity of the medical fluid.

The details of one or more embodiments are set forth in the accompanying drawings and the description below. Other features, objects, and advantages will be apparent from the description and drawings, and from the claims.

DETAILED DESCRIPTION

Figure 1A:
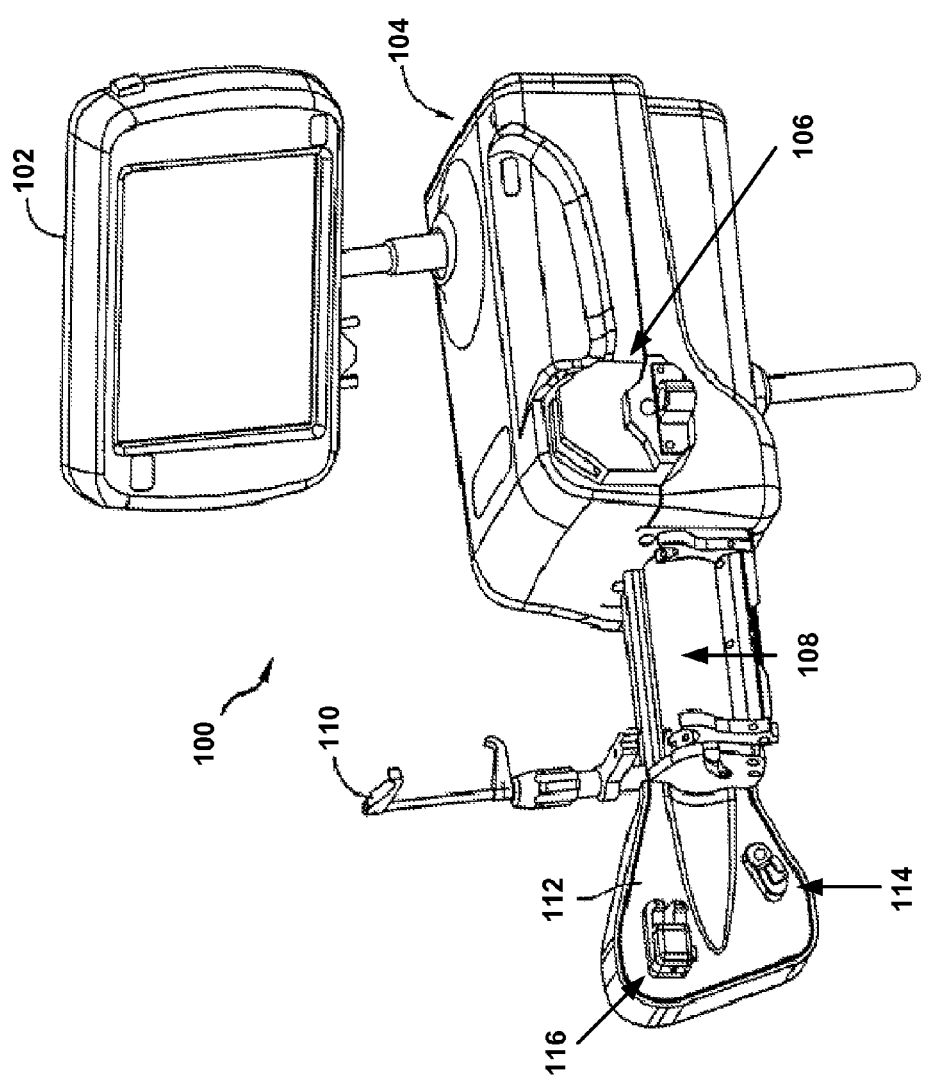
FIG. 1A is a perspective diagram of one embodiment of a powered medical fluid injection device that may be used to implement various aspects of the present invention.

FIG. 1A is a perspective diagram of one embodiment of a powered medical fluid injection device 100 that may be used to implement various aspects of the present invention. In the embodiment of FIG. 1A, the pressurizing unit within sleeve 108 is a syringe. In other embodiments, other forms of pressurizing units may be used, including other types of positive displacement pumps. Device 100 is, in some embodiments, used to inject medical fluid, such as contrast media or saline, into a patient during a medical procedure, such as an angiographic or computed tomography (CT) procedure. Device 100 includes a control panel 102, an injector head 104, a sleeve 108 to hold a pressurizing unit, a reservoir holder 110, a module 112, a patient manifold sensor 114, and an air detector 116.

Figure 3A:
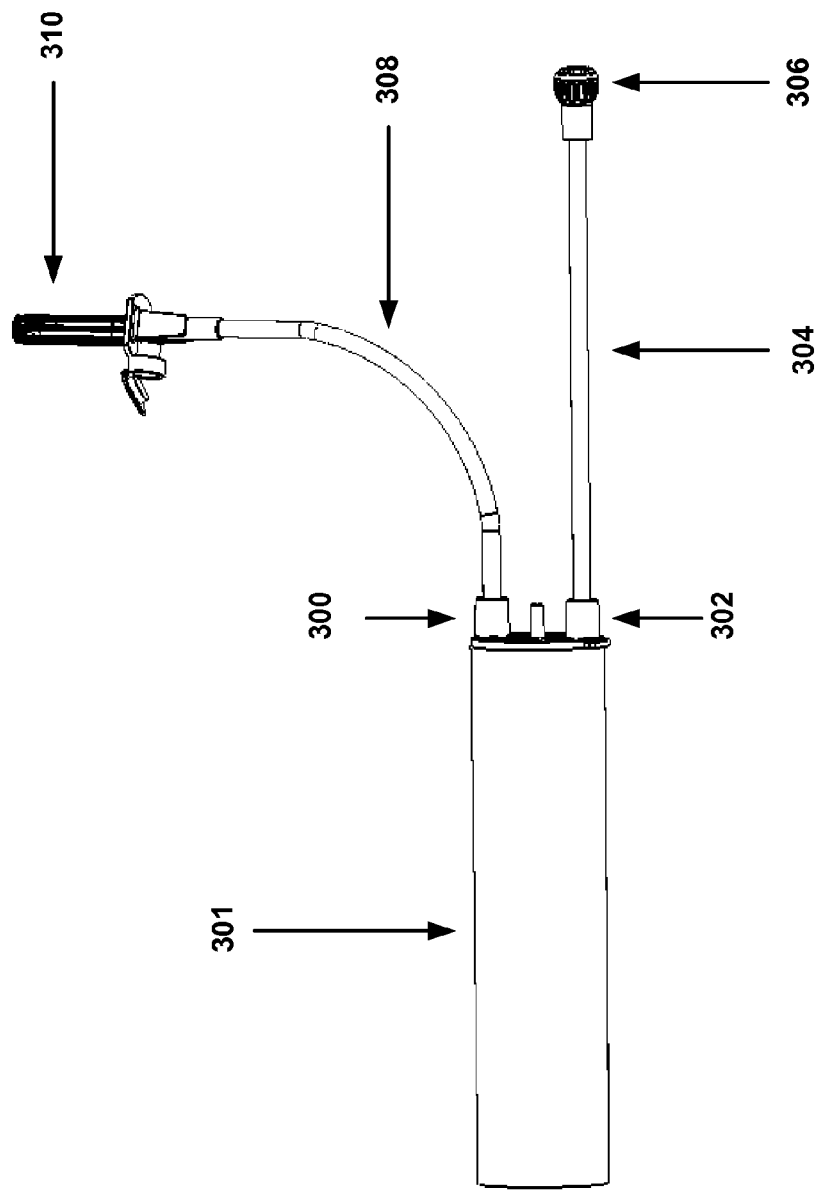
FIG. 3A is a perspective diagram of an example syringe that may be used with a powered medical fluid injection device, according to one embodiment.
Figure 3B:
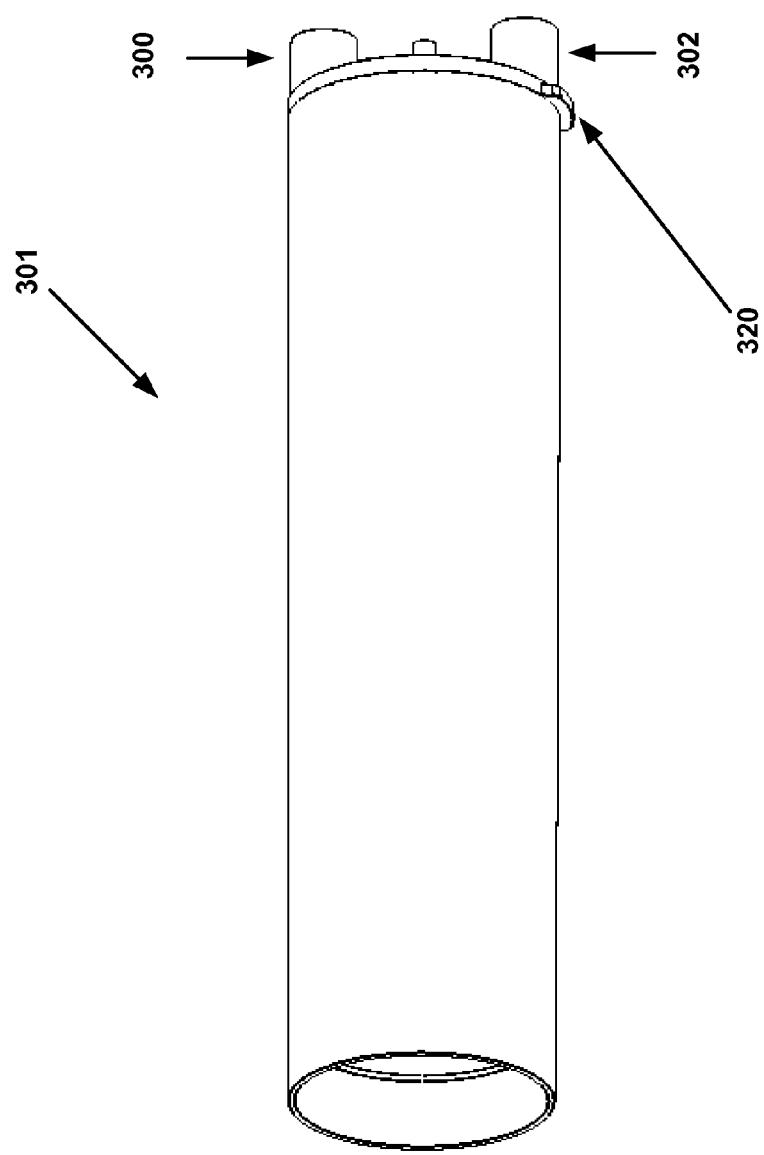
FIGS. 3B-3C are additional perspective diagrams of the example syringe shown in FIG. 3A, the additional perspective diagrams illustrating the example syringe disconnected from any tubing, according to one embodiment.
Figure 3C:
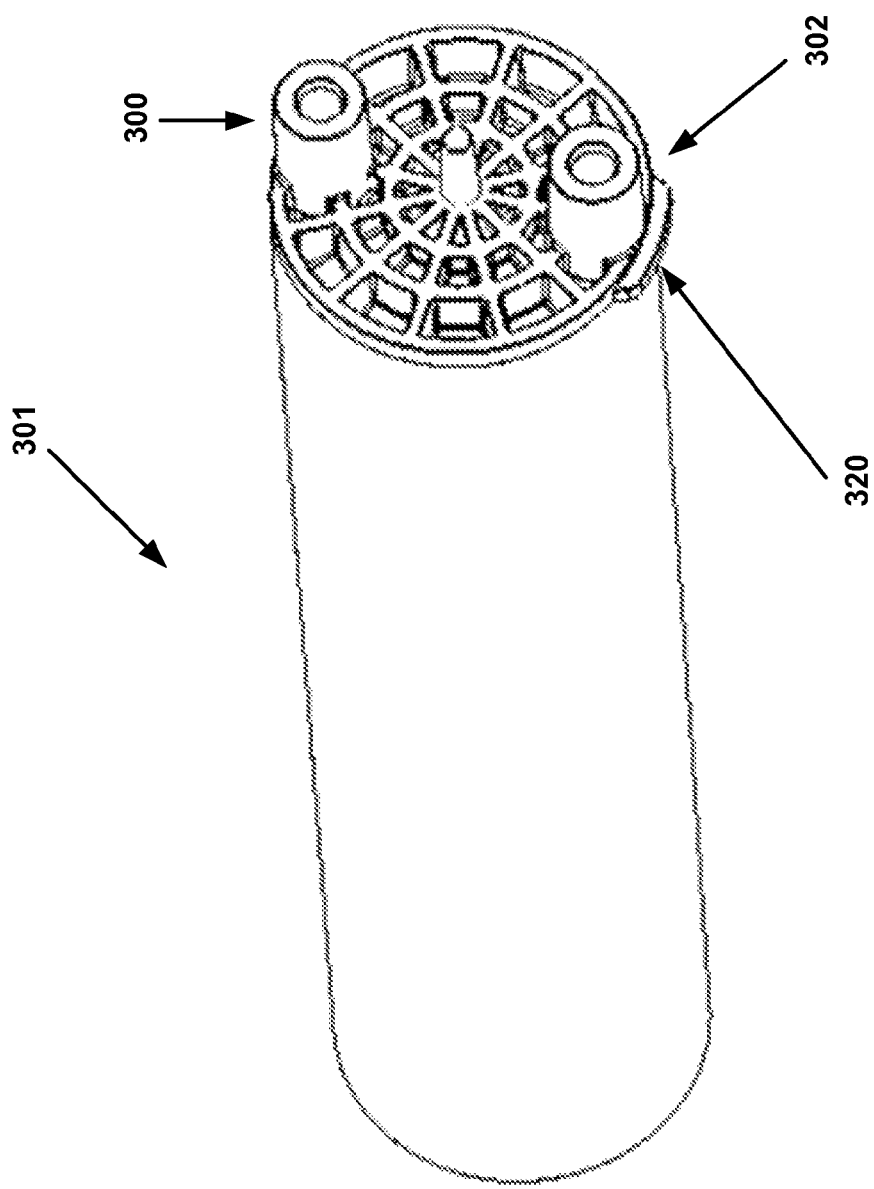

Injector head 104 includes a pump 106 and also includes one or more processors used to control and/or monitor injector head 104, control panel 102, the pressurizing unit within sleeve 108, patient manifold sensor 114, and air detector 116 of device 100. Reservoir holder 110 is capable of holding a fluid reservoir that contains an amount of fluid to be drawn into the syringe during operation of device 100. For example, reservoir holder 110 may hold a reservoir of contrast media or diluent. A second reservoir holder (not shown) may hold a diluent (e.g., saline) for use in pump 106. Patient manifold sensor 114 may, in some cases, be connected to a patient manifold, as will be described in reference to FIG. 1B. FIGS. 3A-3C show examples of a syringe that may be used within sleeve 108, according to one embodiment. Patient manifold sensor 114 may, in some cases, be connected to a patient manifold, as will be described in reference to FIG. 1B.

An operator of device 100, such as a clinician, may use control panel 102 to set up various parameters and/or protocols to be used for a given injection procedure. For example, the operator may interact with control panel 102 to enter injection parameters for flow rate, maximum injection volume, maximum injection pressure, rise time, or other parameters. In one embodiment, control panel 102 includes a touchscreen panel.

Pump 106 is capable of pumping fluid. In one embodiment, pump 106 is a peristaltic pump. In this embodiment, tubing and a fluid reservoir (not shown) are coupled to and through pump 106. Pump 106 pumps fluid from the fluid reservoir through the tubing towards module 112. In the example of FIG. 1A, both pump 106 and the syringe contained within sleeve 108 are capable of delivering fluid from device 100 into a catheter. Pump 106 is driven by a motor that is part of pump 106, and the plunger within the syringe is driven by a motor assembly, including an actuator, that is part of injector head 104. In one embodiment, injector head 104 includes a processor that drives the motor assembly.

In one embodiment, reservoir holder 110 holds a fluid reservoir that is coupled to input fluid tubing. This input fluid tubing is coupled to the syringe, such that when the plunger within the syringe is moved in a first direction by the motor, fluid is drawn from the reservoir into the syringe. The syringe within sleeve 108 is further coupled to output tubing. When the plunger within the syringe is moved in a second, opposite direction, fluid is expelled out of the syringe into the output tubing. In one embodiment, the syringe is a dual-port syringe, such that the input tubing is coupled to one port of the syringe, and the output tubing is coupled to another port of the syringe. FIG. 3A shows an example of such a dual-port syringe, which will be described in more detail below.

Patient manifold sensor 114 is coupled to a manifold valve (not shown), according to one embodiment. This manifold valve controls flow of fluid from tubing coupled to either the syringe in sleeve 108 or pump 106. In one embodiment, the manifold valve is coupled to output tubing from the syringe and also to tubing that runs through pump 106. Tubing also is coupled between the manifold valve and air detector 116. After passing through air detector 116, the tubing is then coupled to a patient line or catheter (not shown), such that fluid can ultimately be delivered from device 100 to a patient.

The manifold valve held by the patient manifold sensor 114 is capable of controlling the flow of fluid from the syringe and pump 106 to an external catheter. In one embodiment, the manifold valve has a first position that allows only fluid from the syringe to be delivered to the catheter. The manifold valve has a second position that allows only fluid from pump 106 to be delivered to the catheter. In one embodiment, the manifold valve may comprise a spring-biased spool valve, but in other embodiments, other types of valves, including check valves, may also be used. Patient manifold sensor 114 can detect the manifold valve position and report this position to injector head 104 for safety purposes.

Device 100 also includes air detector 116. Tubing that runs from device 100 to an external catheter passes through air detector 116, which is capable of detecting air bubbles or air columns within the tubing. If air detector 116 detects a measureable or otherwise significant amount of air within the tubing, it is capable of generating an alarm signal for injector head 104. In such a case, a warning or alarm message may be displayed to the operator on control panel 102, indicating that air has been detected. In addition, in one embodiment, device 100 may automatically pause, or terminate, a fluid injection procedure if air detector 116 has detected air in the tubing, such that the air is not delivered to the catheter.

Device 100 may be used to provide a mating mechanism between sleeve 108 and a pressurizing unit that is to be inserted into sleeve 108, such as syringe 301 shown in FIGS. 3A-3C, according to one embodiment. In this embodiment, the pressurizing unit includes an external tab having a predefined shape and size. (FIGS. 3B-3C, described in more detail below, show such a tab 320 of syringe 301.) Sleeve 108 includes a notch having a substantially identical predefined shape and size. (The notch included in sleeve 108 may be similar to the notch 500 (FIG. 5) or notch 600 (FIG. 6), which are provided in sleeves for device 200 of FIG. 2A.) Because the shape and size of the notch of sleeve 108 is substantially identical to the shape of size of the pressurizing unit's tab, the tab can mate with the notch when the pressurizing unit is inserted into sleeve 108. This mating mechanism may help ensure a proper alignment or positioning of the pressurizing unit within sleeve 108.

Figure 1B:
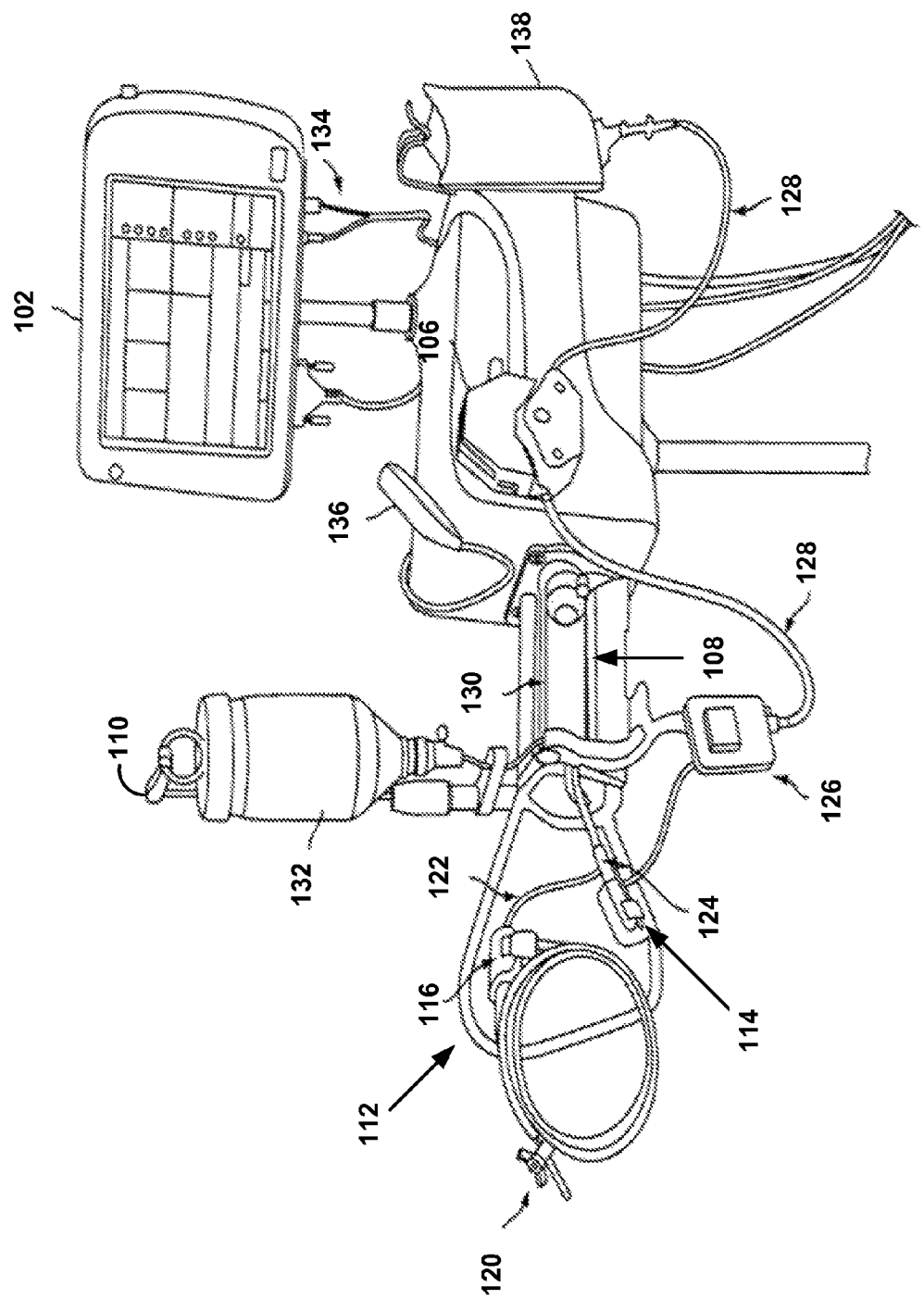
FIG. 1B is a perspective diagram of one embodiment of the powered medical fluid injection device of FIG. 1A connected to various components, including fluid reservoirs and tubing.

FIG. 1B is a perspective diagram of one embodiment of the powered medical fluid injection device 100 of FIG. 1A connected to various components, including fluid reservoirs and tubing. For example, FIG. 1B shows a first fluid reservoir 132 and a second fluid reservoir 138. First fluid reservoir 132 contains a first fluid, such as contrast media. An operator may hang first fluid reservoir 132 on reservoir holder 110. In some cases, first fluid reservoir 132 may be a glass reservoir, while in other cases, it may be a plastic reservoir. The fluid contained within first fluid reservoir 132 may be drawn through tubing and into a pressurizing unit 130 (e.g., a syringe) that has been inserted into sleeve 108 during operation. During an automatic replenishment operation, device 100 may automatically supply pressurizing unit 130 with an amount of fluid from first fluid reservoir 132.

Second fluid reservoir 138 may contain a second fluid, such as saline. An operator may hang second fluid reservoir 138 on a hook 137. In some cases, second fluid reservoir 138 may be a plastic reservoir, such as a bag. The fluid contained within second fluid reservoir 138 may be drawn through tubing 128 through operation of pump 106.

FIG. 1B also shows that a hand-control device 136 is coupled to control panel 102 via a connector 134. In one embodiment, hand-control device 136 may be connected to another component of device 100 other than control panel 102. As shown in FIG. 1B, hand-control device 136 is coupled to tubing, cabling, or wiring, which connects hand-control device 136 to connector 134. Connector 134 may then be connected to or disconnected from control panel 102. An operator may manipulate hand-control device 136 to control injection of fluid from device 100. For example, the operator may use hand-control device 136 as a variable-rate control device to variably control the rate of flow of fluid from device 100 (e.g., flow of fluid out of pressurizing unit 130). In one embodiment, hand-control device 136 may comprise an electrical device. In one embodiment, hand-control device 136 may comprise a pneumatic device.

Tubing 128 is coupled to a pressure transducer 126. Pressure transducer 126 is also coupled to output, high-pressure tubing 122, which may be connected to a patient line via connector 120. When high-pressure tubing 122 is connected to a patient line (within a patient), pressure transducer 126 is capable of functioning as a hemodynamic monitor for the patient. Pressure transducer 126 converts detected pressures into electrical signals that may be monitored or otherwise used by device 100 or another monitoring device. High-pressure tubing 122 also runs through air detector 116. Air detector 116 is capable of detecting the presence of air (e.g., air bubbles or columns) within fluid that may be flowing through high-pressure tubing 122.

FIG. 1B also shows a manifold valve 124. This manifold valve 124 is connected to high-pressure tubing 122, as well as patient manifold sensor 114. Manifold valve 124 is capable of controlling a flow of fluid from pressurizing unit 130 and/or through pump 106 to high-pressure tubing 122. For example, in one embodiment, when manifold valve 124 is in a first position, fluid may flow from pressurizing unit 130 to high-pressure tubing 122. When manifold valve 124, however, is in a second position, fluid may flow through pump 106, via tubing 128, to high-pressure tubing 122. In one embodiment, manifold valve 124 may allow fluid flow to high-pressure tubing 122 from only one of pressurizing unit 130 or pump 106 at a time.

Figure 2A:
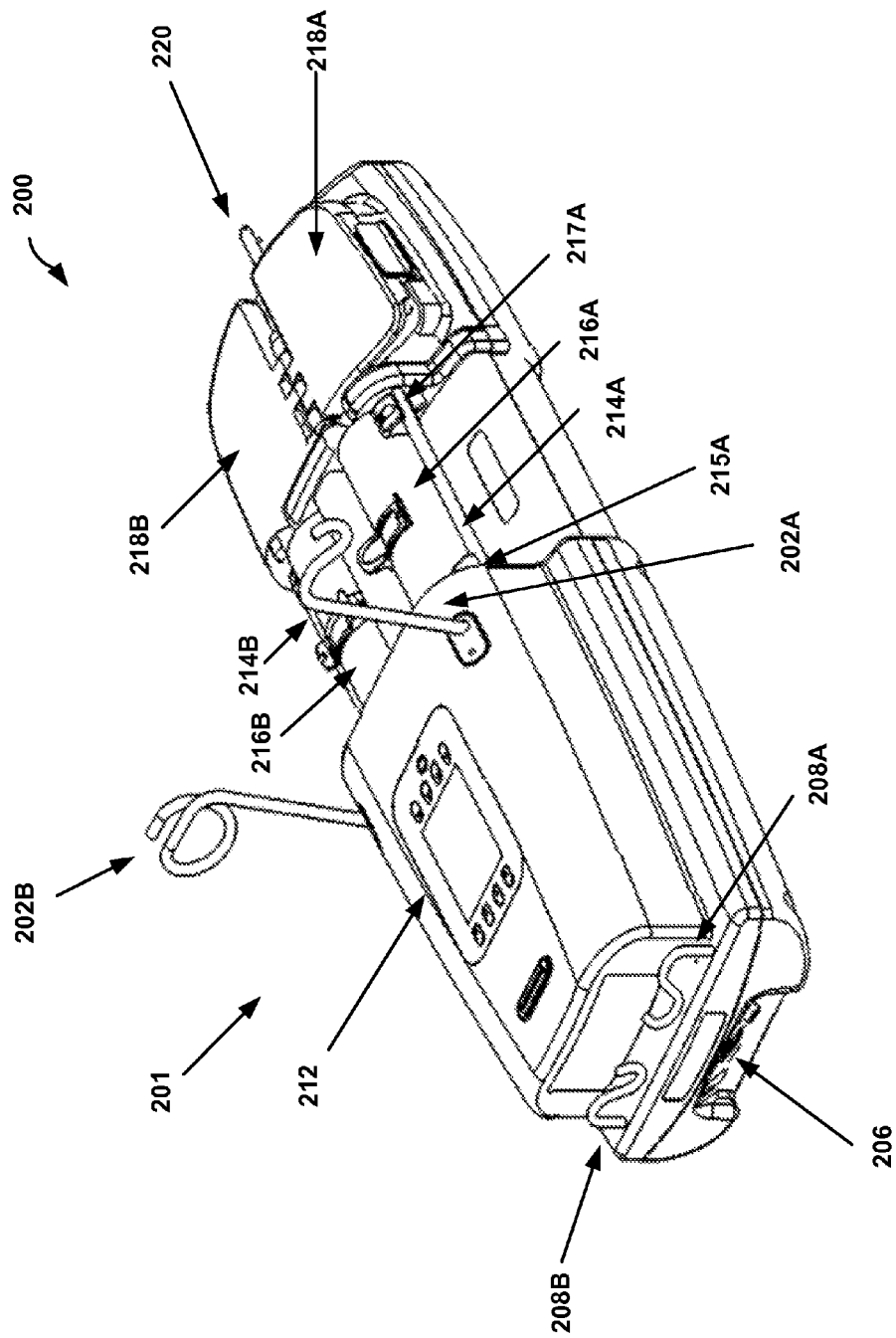
FIGS. 2A-2D are various perspective diagrams of another embodiment of a powered medical fluid injection device that may be used to implement various aspects of the present invention.

FIG. 2A is a perspective diagram of another embodiment of a powered injection device 200 that may be used to implement various aspects of the present invention. In FIG. 2A, device 200 includes a first primary reservoir holder 202A, a second primary reservoir holder 202B, an electrical connection interface 206, a first backup reservoir holder 208A, a second backup reservoir holder 208B, a control panel 212, a first syringe rod 214A, a second syringe rod 214B, a first syringe sleeve 216A, a second syringe sleeve 216B, a first front-end assembly 218A, a second front-end assembly 218B, and a patient connection guide rod 220. In the embodiment of FIG. 2A, the pressurizing units that are used to deliver medical fluid are syringes that are contained within sleeves 216A and 216B. Injector head 201 includes reservoir holder 202A, reservoir holder 202B, connection interface 206, reservoir holder 208A, reservoir holder 208B, and control panel 212. Injector head 201 further includes one or more processors used to control and/or monitor the components of injector head 201 and other components of device 200.

Reservoir holder 202A is capable of holding a first reservoir of medical fluid, while reservoir holder 202B is capable of holding a second reservoir of medical fluid. In one embodiment, reservoir holder 202A holds a reservoir of a first type of fluid, such as contrast media, while reservoir holder 202B holds a reservoir of a second, different type of fluid, such as a diluent (e.g., saline). Different forms of reservoirs (e.g., bottles, bags) may be used with reservoir holders 202A and 202B. Because device 200 may be used to inject medical fluid over multiple patient procedures, the reservoirs held by holders 202A and 202B may need to be replaced over time. Typically, an operator of device 200 manually replaces the reservoirs on holders 202A and 202B. For operator convenience, device 200 additionally includes backup holders 208A and 208B. The operator may store backup fluid reservoirs on holders 208A and 208B. When a reservoir on primary holder 202A or 202B runs empty and needs to be replaced, operator may quickly and easily access a new fluid reservoir from one of backup holders 208A or 208B and attach to primary holder 202A or 202B.

Device 200 includes electrical connection interface 206 to directly or indirectly couple device 200 to an external medical device, such as a medical imaging device. Typically, device 200, when used as a contrast media injection device, works in conjunction with a medical imaging device. For example, device 200 may work in conjunction with a medical imaging device during an angiographic or CT procedure. Connection interface 206 is used to directly or indirectly connect device 200 to such an imaging device. In one embodiment, device 200 may transmit injection and/or control information to an external imaging device via interface 206, and may receive imaging and/or control information from the external imaging device via interface 206, as well.

FIG. 2A shows that device 200 also includes control panel 212. Control panel 212 is located on the top side of example device 200. The operator may interact with control panel 212 to program various injection procedure parameters and/or protocols that may be used for injection procedures. The operator may also use control panel to set up device 200 for use, to begin, pause, resume, or end a procedure, or to view various injection-related information (such as flow rate, volume, pressure, rise time, procedure type, fluid information, and/or patient information). FIG. 2A shows various user-activated buttons on the side of control panel 212. However, in one embodiment, control panel 212 may include a touch-activated screen.

In one embodiment, a separate, larger control panel (not shown) may also be in communication with device 200. In this embodiment, the larger control panel provides similar operator functionality to that provided by control panel 212. However, the larger control panel may be mounted to a rail of a bed on which a patient is lying, or may be mounted to other devices separate from device 200. In one embodiment, the larger control panel looks similar to control panel 102 shown in FIG. 1A.

Device 200 is a dual-syringe device that includes two syringes contained within sleeves 216A and 216B. Both syringes are capable of delivering medical fluid to a patient. Syringe rod 214A, which is part of device 200, couples sleeve 216A to device 200, while syringe rod 214B couples sleeve 216B to device 200. Sleeve 216A includes connectors 215A and 217A which connect sleeve 216A to rod 214A. Connectors 215A and 217A are attached to sleeve 216A, according to one embodiment, and allow sleeve 216A to be attached or removed from rod 214A. In one embodiment, connectors 215A and 217A allow sleeve 216A to be rotated about the axis of rod 214A. Thus, in this embodiment, an operator may rotationally load and unload sleeve 216A from device 200 without detaching sleeve 216A from rod 214A. (FIG. 2A shows sleeve 216A in the loaded position, in which a syringe has been inserted into sleeve 216A.) When the operator wishes to remove the syringe contained within sleeve 216A from device 200, the operator may move sleeve 216A to an unloaded position by rotating it about rod 214A, and may then remove the syringe contained within sleeve 216A by sliding it out of sleeve 216A. If the operator further wishes to remove sleeve 216A from device 200, the operator may detach connectors 215A and 217A from rod 214A (such as by rotating sleeve 216A to an unload position and manually pulling sleeve 216A away from rod 214A). In one embodiment, the syringe contained within sleeve 216A is a disposable component that may be disposed of and replaced after use in one or more patient procedures. (Sleeve 216B includes connectors 215B and 217B (shown in FIG. 2C) which connect sleeve 216B to rod 214B. A separate syringe may be contained within sleeve 216B.)

In one embodiment, the syringe within sleeve 216A is capable of drawing in fluid from a fluid reservoir coupled to holder 202A, and the syringe within sleeve 216B is capable of drawing in fluid from a fluid reservoir coupled to holder 202B. For example, these syringes may draw in fluid during a fluid replenishment operation. Each syringe is coupled to a motor/actuator assembly (not shown) that drives a plunger in one of two directions. During a fluid replenishment cycle, for example, a motor/actuator assembly of device 200 may drive a plunger within the syringe in sleeve 216A in one direction to draw fluid from a reservoir coupled to holder 202A into the syringe. During an injection cycle, the motor/actuator assembly of device 200 may drive the plunger within this syringe in the opposite direction to expel fluid. In one embodiment, device 200 contains two distinct motor/actuator assemblies, such that one assembly drives the syringe within sleeve 216A while another drives the syringe within sleeve 216B. These motor/actuator assemblies are part of injector head 201, and may individually be controlled or monitored by the one or more processors included within injector head 201.

Fluid input tubing couples the syringes within sleeves 216A and 216B to the fluid reservoirs and to output lines, according to one embodiment. In one embodiment, the syringes each are dual-port syringes (such as the dual-port syringe shown in FIG. 3). In this embodiment, one syringe port is used for input tubing that is coupled to a fluid reservoir, while the second port is used for output tubing that is operatively coupled to an output (patient) line through assemblies 218A or 218B.

Front-end assembly 218A is associated with sleeve 216A, and front-end assembly 218B is associated with sleeve 216B. Output tubing from the syringe in sleeve 216A runs through assembly 218A and out to a patient line, while output tubing from the syringe in sleeve 216B runs through assembly 218B and out to the patient line. Each assembly 218A and 218B includes a door, or cover, which may be opened and closed by the operator. For example, the operator may open the door when loading tubing and may close the door upon loading. In one embodiment, each door may be made of a transparent or translucent material, such that the operator may see inside the contents of the assembly 218A or 218B even when the door is closed.

In one embodiment, each front-end assembly 218A and 218B includes air detectors and valve components (not shown). Air detectors are used to detect air bubbles or air columns within the fluid tubing that is used. The valve components are used to allow or restrict fluid flow through tubing. For example, when pinch valves are used, the valves pinch fluid tubing to restrict fluid flow in one state, but stay open to allow fluid flow in another state. Various different forms of valves may be used within assemblies 218A and 218B. In addition, various different forms of air detectors (e.g., ultrasonic, optical) may be used, as well.

In one embodiment, the input and output tubing that is coupled to the syringe in sleeve 216A runs through front-end assembly 218A, and the input and output tubing that is coupled to the syringe in sleeve 216B runs through front-end assembly 218B. In this embodiment, each assembly 218A and 218B contains a first pinch valve and a first air detector coupled to the input tubing for the respective syringe, and further contains a second pinch valve and a second air detector coupled to the output tubing for the respective syringe. These components are more clearly shown in FIG. 2D and will be discussed in more detail below.

Figure 4:
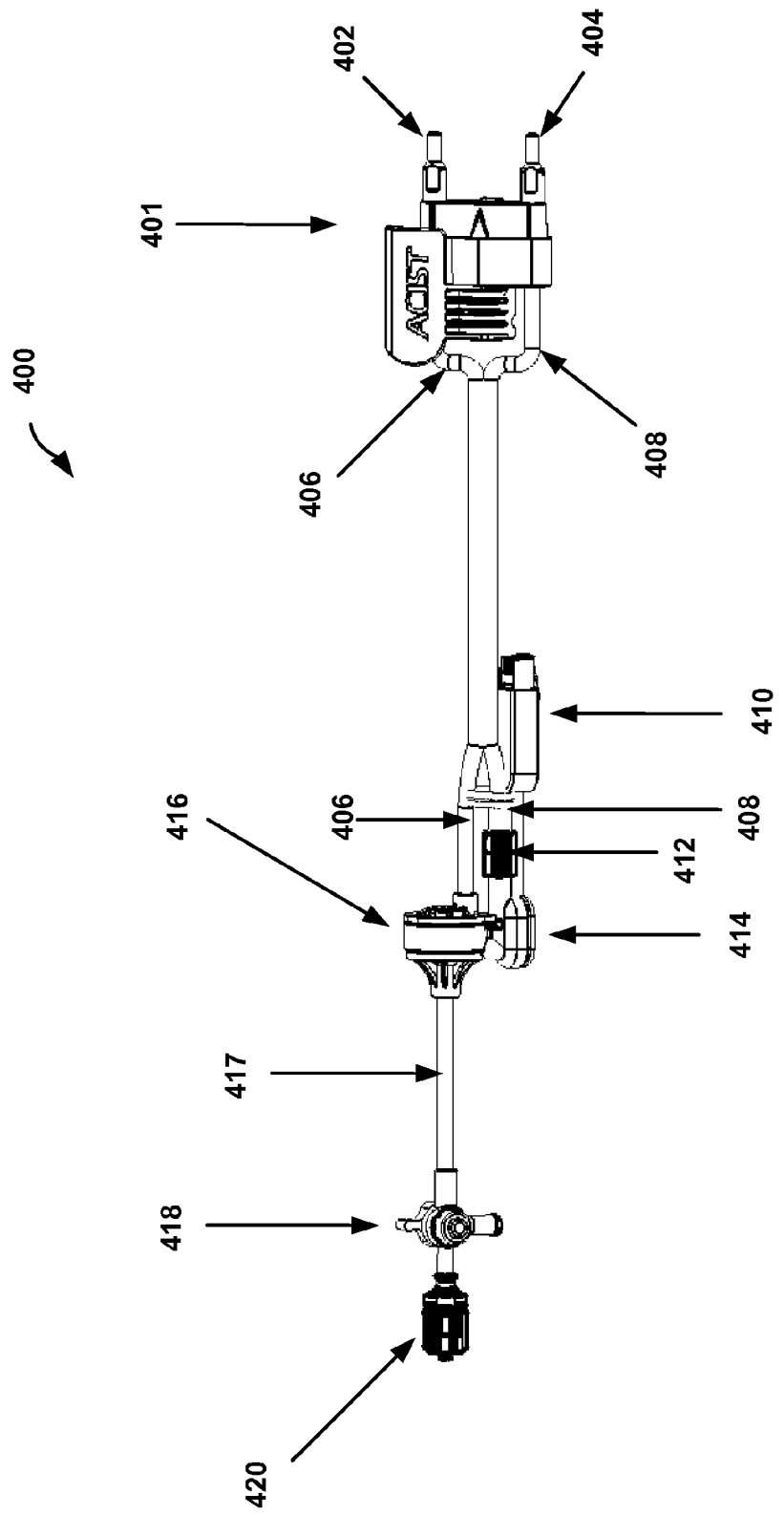
FIG. 4 is a perspective diagram of a patient line that may be used with a powered medical fluid injection device, according to one embodiment.

FIG. 2A also shows a patient connection guide rod 220. The output tubing from syringes 216A and 216B run through front-end assemblies 218A and 218B, respectively, and are then coupled to a patient line, or kit (not shown). The patient line is a single-use line, according to one embodiment, that is used for a single patient procedure. Each patient line may be connected to and disconnected from the output tubing running through front-end assemblies 218A and 218B. The patient line is connected to the output tubing via connection guide rod 220, according to one embodiment. The patient line may slide over connection guide rod 220 in order to become coupled with the output tubing. In one embodiment, the patient line includes two tubing elements, each element corresponding to one of the output tubing elements of the syringe in sleeve 216A or 216B. An example patient line is shown in FIG. 4 and will be discussed in more detail below.

In one embodiment, a medical fluid injection device, such as device 200, may include a plurality of pressurizing units, including three or more pressurizing units. Each of these pressurizing units may be included within a separate sleeve during operation. In some cases, multiple pressurizing units may contain the same type of fluid. For example, a first pressurizing unit may contain contrast media, a second pressurizing unit may contain a diluent (e.g., saline), and a third pressurizing unit may contain contrast media. In this scenario, the third pressurizing unit may comprise a backup, or secondary, source of contrast media. In this example, the first and third pressurizing units may both be coupled to a common front-end assembly, such as a front-end assembly similar to 218A or 218B.

Figure 2B:
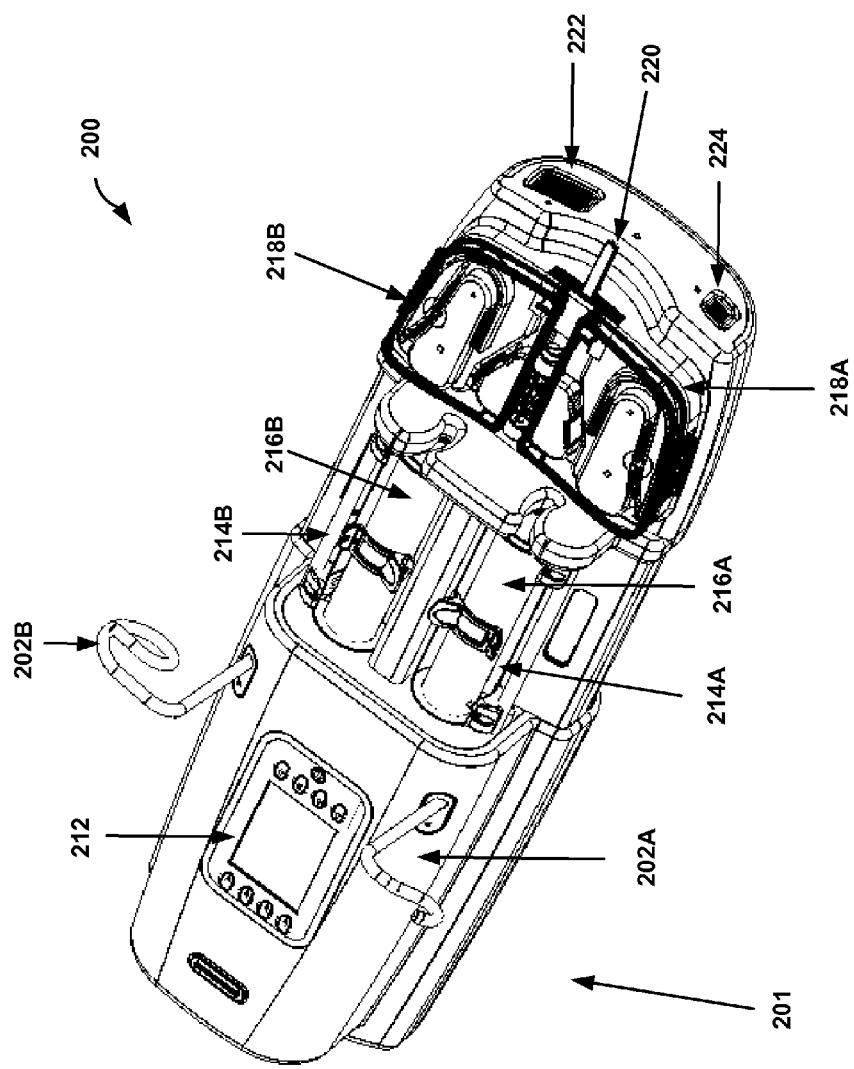

FIG. 2B is another perspective diagram of device 200 shown in FIG. 2A. In FIG. 2B, sleeves 216A and 216B, along with front-end assemblies 218A and 218B, can be more clearly seen. Although the doors of assemblies 218A and 218B are closed in the example of FIG. 2B, they are made of a semi-transparent material, such that the interior pinch valve and air detector components may be more clearly seen. FIG. 2B also shows connection ports 222 and 224. In one embodiment, a pressure transducer connector (such as one coupled to connector 410 shown in FIG. 4), may be connected to connection port 224. The pressure transducer connector is operatively coupled to a pressure transducer, which measures patient hemodynamic signals on the patient line. By connecting a pressure transducer to connection port 224, device 200 is capable of utilizing and processing hemodynamic pressure signals of a patient that are detected in the patient line.

Device 200 also includes connection port 222, which may be connected to a hand-control device (not shown). In one embodiment, the hand-control device is a disposable component that may be used by the operator for a single patient procedure. The hand-control device may control the operation of one or both of syringes in sleeves 216A and 216B. For example, the operator may push a button or otherwise interact with the hand-control device to cause a motor/actuator assembly to inject fluid from the syringe in sleeve 216A, and may push another button or otherwise interact with the hand-control device to cause a motor/actuator assembly to inject fluid from the syringe in sleeve 216B. Thus, if the syringe in sleeve 216A contains contrast media, and the syringe in sleeve 216B contains a diluent, the operator may push one button on the hand-control device to inject contrast into the patient line, and may push another button to inject saline. In one embodiment, the hand-control device contains variable-rate functionality, such that the harder the operator pushes on a button or actuates a component, the greater the flow rate of injected fluid from the syringe in sleeve 216A or 216B.

Figure 2C:
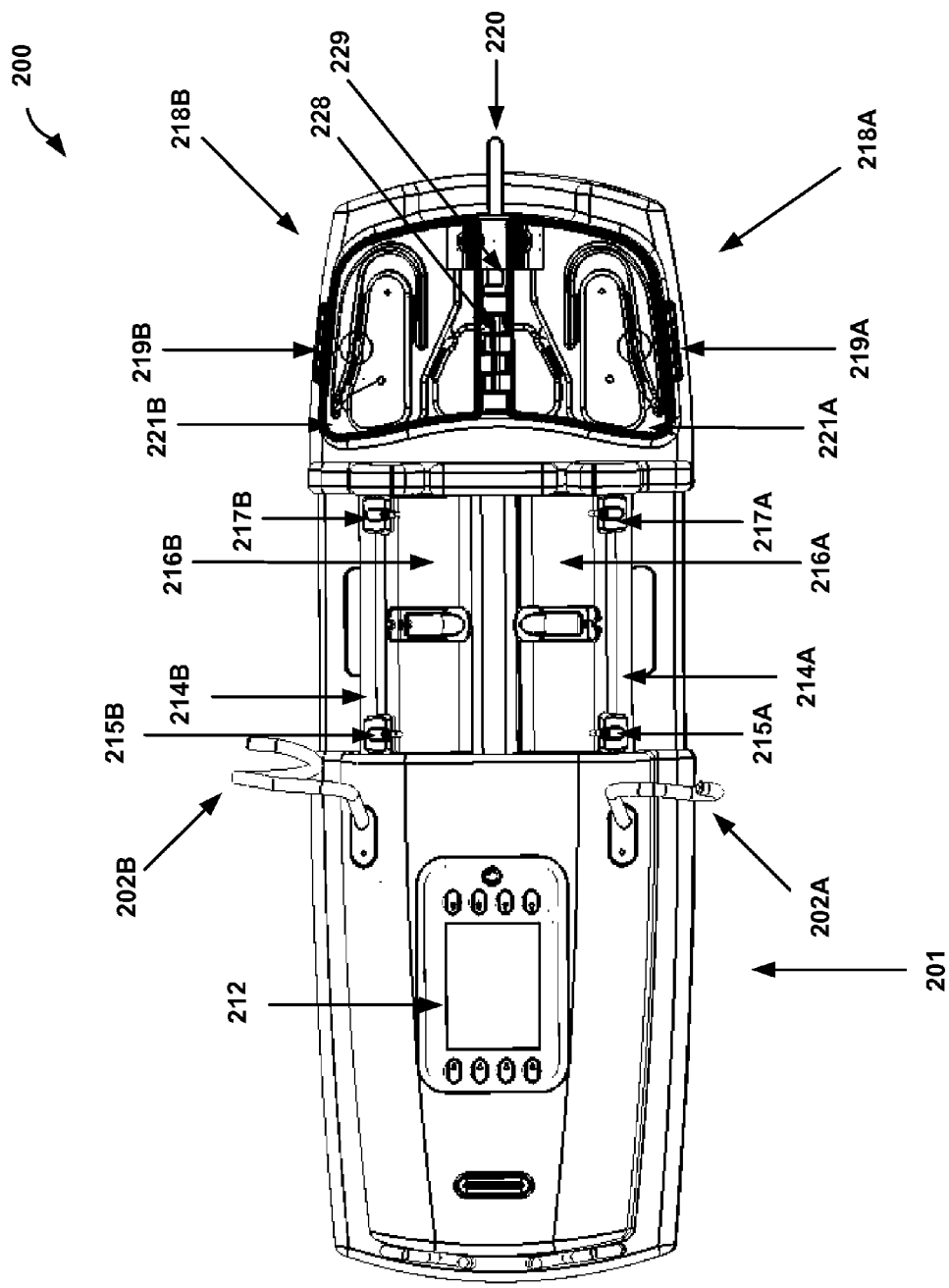

FIG. 2C is another perspective diagram of device 200. FIG. 2C shows a top view of device 200, according to one embodiment. Connectors 215A, 215B, 217A, and 217B are more clearly shown in FIG. 2C. Connectors 215A and 217A couple sleeve 216A to rod 214A. In one embodiment, connectors 215A and 217A are coupled and attached to sleeve 216A, and are releasably coupled to rod 214A. The operator may rotate sleeve 216A about an axis defined by rod 214A to load and unload sleeve 216A. FIG. 2C shows sleeve 216A in an example loaded position, wherein fluid may be drawn into or expelled from the syringe contained within sleeve 216A. The operator may rotate sleeve 216A about the axis of rod 214A and into an unloaded position, at which point the operator may also pull on sleeve 216A to release connectors 215A and 217A from rod 214A. The operator may wish to do so, for example, to replace sleeve 216A with a new sleeve, or to clean sleeve 216A. The operator may use connectors 215A and 217A to re-attach sleeve 216A onto rod 214A. (In a similar fashion, connectors 215B and 217B couple sleeve 216B to rod 214B.)

FIG. 2C also shows doors 221A and 221B on front-end assemblies 218A and 218B, respectively. As noted above, in one embodiment, each of assemblies 218A and 218B include a moveable door 221A and 221B, respectively. Door 221A covers assembly 218A, and door 221B covers assembly 218B. In the embodiment of FIG. 2C, doors 221A and 221B are made of a transparent, or semi-transparent, material, such that an operator may see the contents of assemblies 218A and 218B (which are shown in more detail in FIG. 2D). Door 221A includes a handle 219A, and door 221B includes a handle 219B. The operator may utilize handles 219A and 219B to open and close doors 221A and 221B, respectively. Doors 221A and 221B are coupled to one or more hinges 228, which allow doors 221A and 221B to be opened and closed.

Also shown in FIG. 2C is a pivot pin 229. Pivot pin 229 is inserted through hinges 228, according to one embodiment, to securely allow doors 221A and 221B to be freely opened and closed by an operator. Doors 221A and 221B pivot about an axis that runs through pivot pin 229.

In one embodiment, pivot pin 229 is screwed into place. Pivot pin 229 may also be removed by an operator. For example, the operator may unscrew pivot pin 229 and remove it from front-end assemblies 218A and 218B. After pivot pin 229 has been removed, doors 221A and 221B may also be removed from assemblies 218A and 218B. For example, the operator may choose to remove doors 221A and 221B if the operator wishes to clean or replace doors 221A and 221B.

Figure 2D:
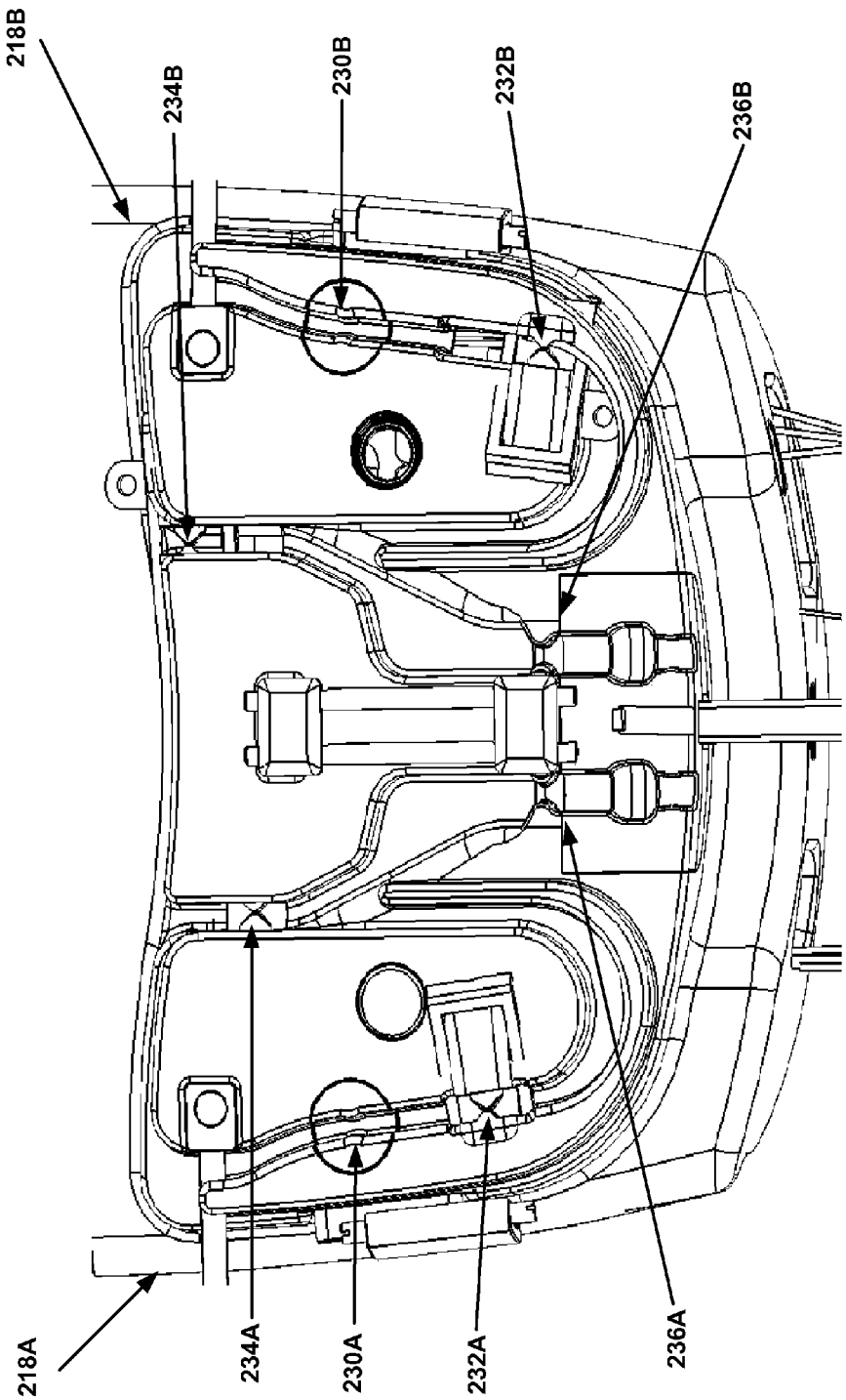

FIG. 2D is a perspective view of front-end assemblies 218A and 218B shown in more detail, according to one embodiment. Although doors 221A and 221B are not shown in FIG. 2D, they are made of a transparent, or semi-transparent, material, such that the contents of assemblies 218A and 218B may be more clearly seen by an operator, even when doors 221A and 221B are closed.

Front-end assembly 218A includes a first air detector 230A, a first pinch valve 232A, a second pinch valve 234A, and a second air detector 236A. Input tubing from a reservoir on holder 202A runs through air detector 230A and pinch valve 232A and into a syringe in sleeve 216A via a first syringe port, according to one embodiment. Output tubing coupled to a second syringe port of the syringe in sleeve 216A runs through pinch valve 234A and air detector 236A and is then coupled an external patient line, or kit (such as the one shown in FIG. 4). Air detector 230A is used to detect air bubbles or columns within the input tubing, and air detector 236A is used to detect air bubbles or columns within the output tubing. Air detectors 230A and 236A may comprise acoustic-based, optical-based, or other forms of air detectors. If either or both of air detectors 230A and 236A detect a measurable amount of air in the input and/or output tubing, these detectors may propagate signals to injector head 201 of device 200. One or more processors of injector head 201 may process these received signals. Injector head 201 may provide a warning message or alert to the operator via control panel 212, such that the operator may take appropriate action. Injector head 201 may also, in one embodiment, automatically pause or terminate any injection of fluid from the syringe in sleeve 216A if air has been detected in the input and/or output tubing, by controlling operation of the motor/actuator assembly driving the syringe.

Pinch valve 232A controls a flow of fluid from input tubing into the syringe in sleeve 216A. Injector head 201 controls the operation of pinch valve 232A. When injector head 201 opens pinch valve 232A, fluid may flow from the reservoir connected to holder 202A and into the syringe. When pinch valve 232A is closed, no fluid flow is permitted within the input tubing. For example, when injector head 201 is supplying the syringe with fluid, it may open pinch valve 232A to allow fluid flow in the input tubing, but it may also close pinch valve 234A, to prohibit any fluid flow in the output tubing. The plunger within the syringe may be moved in a first direction (by the motor/actuator assembly) to supply fluid to the syringe. When a fluid injection occurs, the motor/actuator assembly will move the plunger within the syringe in a second, opposite direction. Injector head 201 may close pinch valve 232A during an injection procedure, to prohibit fluid flow in the input tubing. However, injector head 201 may open pinch valve 234A, to allow fluid flow in the output tubing during such a procedure. In such fashion, injector head 201 utilizes pinch valves 232A and 234A to control fluid flow in the input and output tubing during various operations (e.g., replenishment and injection operations).

In one embodiment, pinch valves 232A and 234A are solenoid-based pinch valves. In other embodiments, other forms of pinch valves 232A and 234A may be used, such as pneumatic-based valves. In one embodiment, pinch valves 232A and 234A have default states in the closed position. Thus, when device 200 is neither supplying fluid into nor injecting fluid from the syringe in sleeve 216A, both pinch valves 232A and 234A are closed. Pinch valves 232A and 234A may then be opened by device 200 when energy is actively applied to pinch valves 232A and/or 234A. When no energy is applied to pinch valves 232A and/or 234A, they return to a default, closed position. Thus, if there are any power failures to device 200, valves 232A and 234A will return to closed position. This may help improve the safety of device 200.

Similarly, front-end assembly 218B includes a first air detector 230B, a first pinch valve 232B, a second pinch valve 234B, and a second air detector 236B. Input tubing from a reservoir connected to holder 202B runs through air detector 230B and pinch valve 232B and into a first syringe port of the syringe in sleeve 216B. Output tubing coupled to a second syringe port of the syringe runs through pinch valve 234B and air detector 236B, and may then be coupled to a patient line. The components within device 218B function similarly to those contained within device 218A as described above, according to one embodiment.

In one embodiment, device 200 of FIGS. 2A-2D is capable of providing a mating mechanism between sleeves 216A and 216B, and corresponding pressurizing units that are inserted into these sleeves. As will be described in further detail below in reference to FIGS. 3A-3C and FIGS. 5-6, sleeves 216A and 216B, in one embodiment, each include a notch having a predefined shape and size. Pressurizing units that may be used have tabs with predefined shapes and sizes, as well. An operator is able to insert a first pressurizing unit into sleeve 216A when the tab of the first pressurizing unit has a shape and size that are substantially identical to the shape and size of the corresponding notch in sleeve 216A. Similarly, the operator is able to insert a second pressurizing unit into sleeve 216B when the tab of second pressurizing unit has a shape and size that are substantially identical to the shape and size of the corresponding notch in sleeve 216B.

The mating mechanism provided by the notch-tab combination allows the operator to properly identify which pressurizing unit is to be inserted into a corresponding sleeve 216A or 216B. This may be particularly useful when sleeves 216A and 216B receive different types of pressurizing units. For example, sleeve 216A may be configured to receive a pressurizing unit containing saline, while sleeve 216B may be configured to receive a pressurizing unit containing contrast media. In one embodiment, the mating mechanism allows the operator to insert a syringe of saline into sleeve 216A and a syringe of contrast media into sleeve 216B.

In some instances, it may be desirable for the notch-tab configuration (e.g., shape, size) to be substantially similar on both sides of a dual-syringe device, such as device 200. This may allow, for example, the use of a single syringe design that could be used in either syringe sleeve 216A or 216B (e.g., notch 500 could be substantially similar to notch 600). In these instances, a mating of the notch-tab combination may help ensure a proper alignment or positioning of a syringe within sleeve 216A or 216B. In other cases, it may be preferable to have the notch-tab configuration be specific to a particular syringe sleeve. This might be desirable, for example, if pre-filled syringes are to be loaded into the syringe sleeves. In this case, having distinct notch-tab configurations may prevent loading a contrast-filled syringe into the saline syringe sleeve, for example, or vice versa.

In one embodiment, pressurizing units have tabs with shapes and sizes substantially different than the shape and size of a sleeve notch are not allowed to be inserted into that sleeve. For example, if sleeve 216A is configured to receive a pressurizing unit containing saline, the operator would not be able to insert a pressurizing unit containing contrast media into sleeve 216A if this pressurizing unit has a tab with a shape and size that are substantially different from the shape and size of the notch in sleeve 216A. By prohibiting the insertion of such a pressurizing unit into sleeve 216A, device 200 protects against the operator inadvertently trying to insert the wrong type of unit into sleeve 216A.

In addition, device 200 allows sleeves 216A and 216B to be completely removed from device 200. The operator may wish to completely remove one or both of sleeves 216A and 216B if they need to be cleaned or replaced, for example. In one example, the operator may remove sleeve 216A by first rotating sleeve 216A on rod 214A from a loaded position (shown in FIGS. 2A-2C) into an unloaded position. The operator may do so by rotating sleeve 216A around rod 214A away from device 200. Then, the operator may pull on sleeve 216A to detach its connectors 215A and 217A from rod 214A.

FIG. 3A is a perspective diagram of an example syringe 301 that may be used within device 200, according to one embodiment. Syringe 301 may be loaded in either sleeve 216A or 216B. If syringe 301 is loaded into sleeve 216A, it may be coupled to a fluid reservoir connected to holder 202A (FIG. 2A), and may further be coupled to a patient line (FIG. 4).

Syringe 301 is a dual-port syringe in the example of FIG. 3. Input port 300 is coupled to input tubing 308, and output port 302 is coupled to output tubing 304. Input tubing is coupled to a connector 310, which may be connected to a fluid reservoir in holder 202A, assuming syringe 301 is loaded into sleeve 216A. For example, if connector 310 is a spike, the spike may be inserted into a bottle of medical fluid connected to holder 202A. Output tubing 304 is coupled to a connector 306, which couples output tubing 304 to a separate patient line. In one embodiment, connector 306 is a Luer-type connector.

Fluid is drawn from the fluid reservoir into port 300 of syringe 301 via input tubing 308. Fluid is expelled from port 302 of syringe 301 into output tubing 304. Input tubing 308 may run through air detector 230A and pinch valve 232A (FIG. 2D) of front-end assembly 218A, which was described in more detail above, while output tubing 304 may run through pinch valve 234A and air detector 236A. In one embodiment, syringe 301, along with input tubing 308, connector 310, output tubing 304, and connector 306, are disposable, multi-use components. That is, these components may be used within device 200 over multiple uses or patient procedures before they are disconnected from device 200 and disposed of. In another embodiment, these components are disposable, single-use components, meaning that they are disposed of after a single patient procedure.

In one embodiment, syringe 301 may also be used in device 100 (FIG. 1A). When used in device 100, connector 310 would be connected to a fluid reservoir on holder 110, and output tubing 304 would run through patient manifold sensor 114.

FIGS. 3B-3C are additional perspective diagrams of the example syringe 301 shown in FIG. 3A, the additional perspective diagrams illustrating the example syringe 301 disconnected from any tubing, according to one embodiment. Ports 300 and 302 are shown in these figures. In addition, an external tab 320 of syringe 301 is further shown. Tab 320 is coupled to an outer surface of syringe 301, and has a predefined shape and size. In the example of FIGS. 3B-3C, tab 320 is an elongated, rectangular-shaped tab in cross section. In other embodiments, however, tab 320 may have many different sizes and shapes. For example, tab 320 may be a squared-shaped, circular-shaped, triangle-shaped, or other shaped tab in cross section. In addition, tab 320 may have varying sizes.

Figure 5:
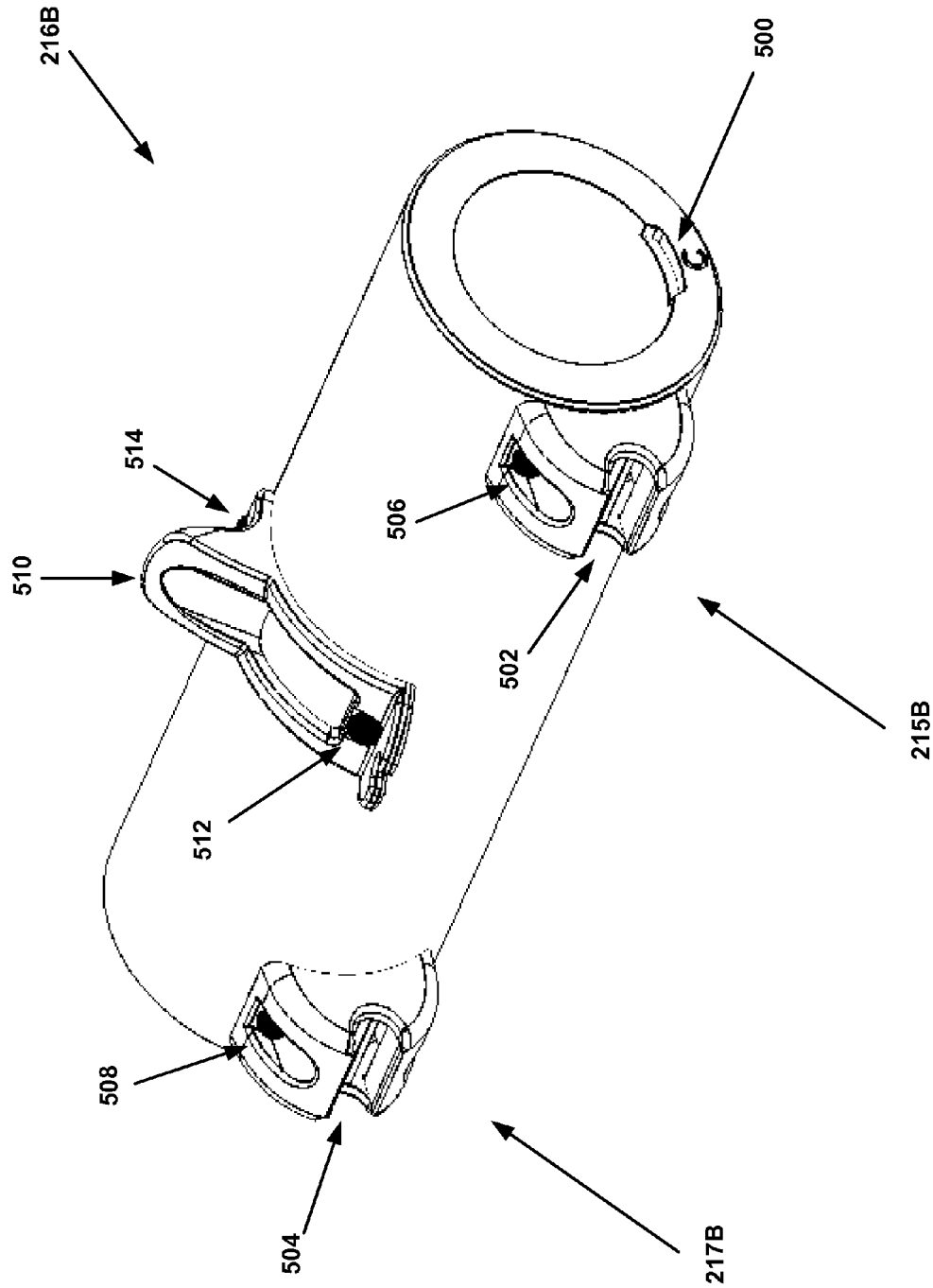
FIG. 5 is a perspective diagram of a syringe sleeve that is used to hold a syringe containing contrast media, according to one embodiment.
Figure 6:
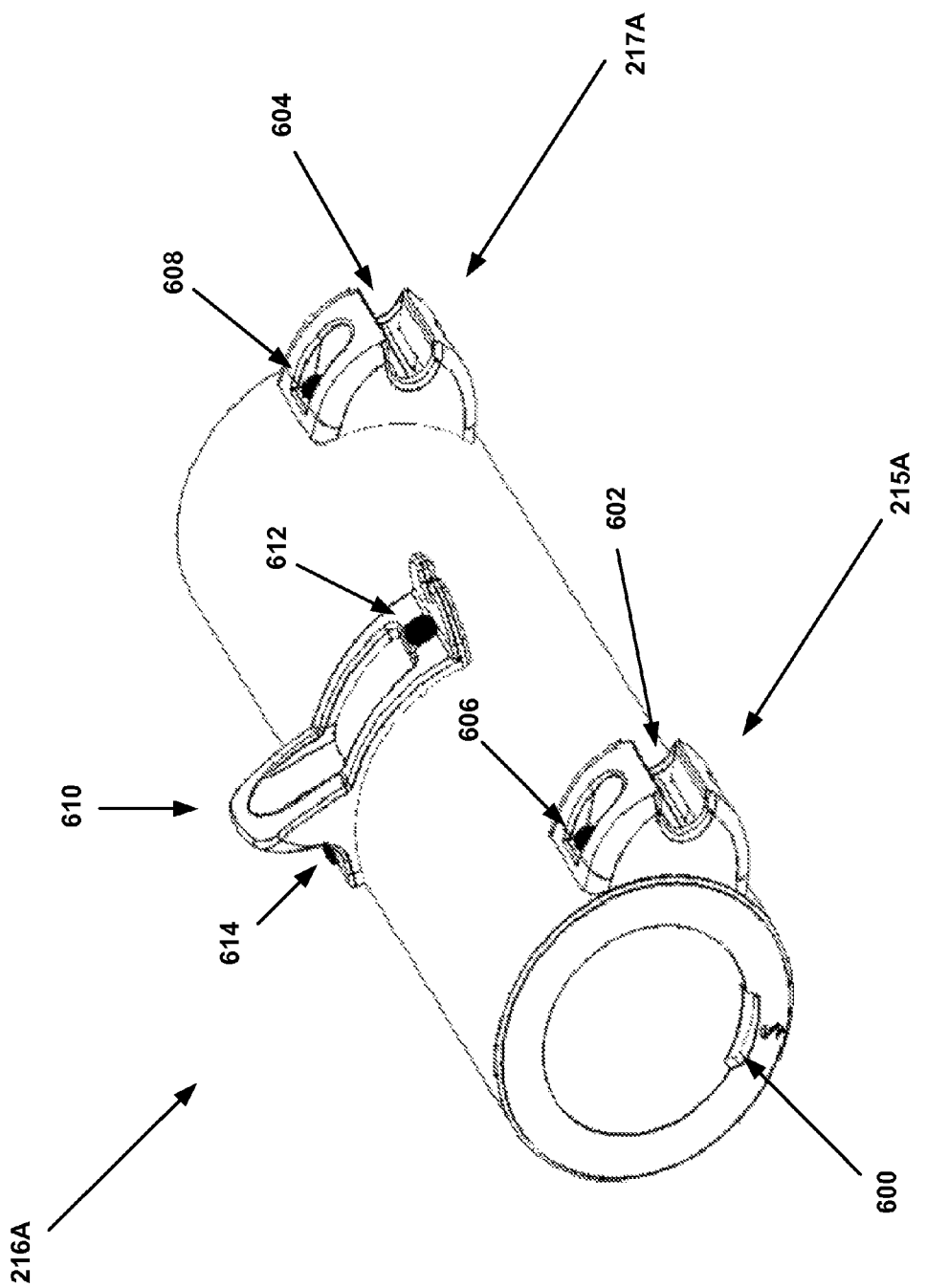
FIG. 6 is a perspective diagram of a syringe sleeve that is used to hold a syringe containing saline, according to one embodiment.

In certain embodiments, tab 320 of syringe 301 is used as part of a mating mechanism when loading syringe 301 within a syringe sleeve, such as sleeve 108 (FIG. 1A), sleeve 216A (FIG. 2A), or sleeve 216B (FIG. 2A). In these embodiments, the syringe sleeve that contains syringe 301 has a corresponding notch having a shape similar to the shape of tab 320. The corresponding notch has a predefined shape and size that are substantially identical to the predefined shape and size of tab 320. The mating mechanism operates similar to a lock-and-key approach, in which the shape and size of the notch in the syringe sleeve allows syringe 301 having a correspondingly shaped and sized tab 320 to be inserted, or loaded, into the sleeve. As such, tab 320 comprises a mating member of syringe 301, and the notch of the syringe sleeve comprises a mating member of the syringe sleeve. FIGS. 5-6 show examples of sleeves 216A and 216B that contain notches having shapes and sizes similar to those of tab 320 shown in FIGS. 3B-3C (such as, for example, substantially identical rectangular shapes in cross section).

In certain embodiments, the mating mechanism may provide for a proper alignment, or positioning, of syringe 301 within a corresponding sleeve. For instance, a mating of tab 320 and a notch of the corresponding sleeve may allow for a proper alignment or positioning of syringe 301 within the sleeve, given that the notch and tab 320 may have a substantially identical shape and size in the context of a lock-and-key type mating mechanism. In some instances, proper alignment or positioning of syringe 301 within the corresponding sleeve may provide for a proper alignment or positioning of ports 300 and 302. For example, once syringe 301 is properly aligned or positioned within its sleeve, and the sleeve is then rotated or otherwise loaded into position within device 200, an operator may be able to properly and quickly connect input tubing 308 to port 300, for example, and to connect output tubing 304 to port 302. In some instances, ports 300 and 302 may need to be oriented in a certain manner upon loading of the sleeve into device 200, such that tubing 308 and 304 may be properly installed and connected to syringe 301. The use of tab 320 and its mating notch within the sleeve may assist in providing a proper alignment or positioning of syringe 301 within the sleeve to ensure that ports 300 and 302 are oriented properly, according to one embodiment.

FIG. 4 is a perspective diagram of a patient line 400 that may be used with injection device 200 shown in FIGS. 2A-2C, according to one embodiment. Patient line 400 includes an assembly 401, a valve 416, a stopcock 418, and a connector 420. Patient line 400 is used to couple device 200 with a catheter that is used to deliver medical fluid to a patient.

Assembly 401 includes a first connector 402 and a second connector 404. When assembly 401 is coupled to device 200, connector 402 is connected with a connector for output tubing that is coupled to one of the syringes in sleeves 216A or 216B, while connector 404 is connected with a connector for output tubing that is coupled to the other syringe. For example, connector 402 may be connected to connector 306 (FIG. 3), which is coupled to output tubing 304 for the syringe in sleeve 216A. Patient line 400 is a disposable kit, in one embodiment, such that connectors 402 and 404 may be connected to and removed from tubing connectors, such as connector 306, by the operator. In one embodiment, patient line 400 is a single-use disposable kit, such that it is connected to device 200 for one patient use, and then subsequently disconnected and discarded.

Connector 402 is operatively coupled to tubing 406, and connector 404 is operatively coupled to tubing 408. In one embodiment, connector 402 is coupled to the syringe in sleeve 216A, which contains contrast media, while connector 404 is coupled to the syringe in sleeve 216B, which contains a diluent such as saline. Thus, in this embodiment, contrast media is injected into tubing 406 of patient line 400, while diluent is injected into tubing 408. Tubing 406 and 408 are coupled to valve 416, which, in one embodiment, comprises an elastomeric-type valve that allows fluid flow from only one of tubing 406 and 408 to output tubing 417. In one embodiment, valve 416 comprises a one-way valve that allows fluid flow only in the direction towards output tubing 417. Guide rod 220 may help, in some cases, maintain the sterility of connectors 402 and 404 by aligning these connectors, during insertion, to prevent contact with non-sterile items.

As is shown in FIG. 4, tubing 408 is coupled to check valve 412 and transducer 414. In one embodiment, check valve 412 comprises a bi-directional check valve. Transducer 414 comprises a pressure transducer in one embodiment that is capable of measuring hemodynamic signals of a patient when patient line 400 is coupled a catheter that has been inserted into the patient. Transducer connector 410 may be coupled to device 200, such as by way of port 224 (FIG. 2B). When connected, hemodynamic signals generated by transducer 414 may be processed by a processor within device 200.

Output tubing 417 is coupled to stopcock 418 and to connector 420 shown in FIG. 4. Stopcock 418 may be manually manipulated by the operator to control fluid flow, and may also be connected to other external devices, such as a syringe. Connector 420 is used to connect patient line 400 to an external catheter that may deliver fluid to a patient. In one embodiment, connector 420 comprises a Luer-type connector.

In one embodiment, patient line 400 may also be used with device 100 shown in FIG. 1A. When used with device 100, transducer connector 410 is coupled to a mating port within device 100 (not shown), such that a processor of device 100 may process the hemodynamic signals. Assembly 401 may also be coupled in device 100 in this embodiment. Patient line 400 may be coupled to a manifold valve that is coupled to patient manifold sensor 114, such that connection port 402 may be coupled to tubing from the syringe, while connection port 404 may be coupled to tubing running through pump 106. In this embodiment, tubing 417 may also be coupled to, or run through, air detector 116 of device 100.

FIG. 5 is a perspective diagram of a syringe sleeve that is used to hold a syringe containing contrast media, according to one embodiment. In this embodiment, syringe sleeve 216B (FIG. 2) is intended to hold a syringe of contrast media. Sleeve 216B includes a notch 500. In the example of FIG. 5, the letter "C" is printed on sleeve 216B adjacent to notch 500. This letter "C" is a symbol for contrast media. An operator may use the visual indication provided by this letter "C" to determine that sleeve 216B is to contain a syringe having contrast media. The letter "C" specifies the type of syringe that is to be inserted into sleeve 216B.

Sleeve 216B includes connectors 215B and 217B. Connector 215B includes a groove 502 and a screw 506. Connector 217B includes a groove 504 and a screw 508. Grooves 502 and 504 couple sleeve 216B to rod 214B (FIG. 2). Screws 506 and 508 attach connectors 215B and 217B, respectively, to an outer surface of sleeve 216B. An operator may unscrew screws 506 and 508 to detach connectors 215B and 217B, respectively, from sleeve 216B. In some embodiments, connectors 215B and 217B may be integrally molded as part of sleeve 216B.

In one embodiment, connectors 215B and 217B comprise snap connectors that may snap onto or snap off of rod 214B. For example, the operator may push sleeve 216B towards rod 214B to snap connectors 215B and 217B onto rod 214B. The operator may also pull sleeve 216B away from rod 214B to snap connectors 215B and 217B off rod 214B to completely detach sleeve 216B from rod 214B.

Sleeve also includes a handle 510. Handle 510 is secured to the outer surface of sleeve 216B by screws 512 and 514. The operator may place one or more fingers on handle 510 to move sleeve 216B on device 200. For example, the operator may use handle 510 to rotate sleeve 216B on rod 214B into either a loaded position (shown in FIG. 2) or an unloaded position. When sleeve 216B is in the loaded position, it typically contains a syringe having fluid that may be injected by device 200. When sleeve 216B is in the unloaded position, the operator may insert or remove a syringe, such as syringe 301, from sleeve 216B. Often, sleeve 216B may be in the unloaded position after fluid in the syringe (which was previously inserted into sleeve 216B) has been injected by device 200.

FIG. 6 is a perspective diagram of a syringe sleeve that is used to hold a syringe containing saline, according to one embodiment. In this embodiment, sleeve 216A holds such a syringe. FIG. 6 shows connectors 215A and 217A, and also a handle 610, which are similar to the corresponding components shown in FIG. 5. Connector 215A includes a groove 602 and a screw 606, and connector 217A includes a groove 604 and a screw 608. Screws 606 and 608 attach connectors 215A and 217A, respectively, to an outer surface of sleeve 216A, and grooves 602 and 604 allow sleeve 216A to be rotated on or around rod 214A, particularly when an operator manipulates handle 610 of sleeve 216A. Handle 610 is attached to the outer surface of sleeve 216A using screws 612 and 614.

In one embodiment, connectors 215A and 217A comprise snap connectors that may snap onto or snap off of rod 214A. For example, the operator may push sleeve 216A towards rod 214A to snap connectors 215A and 217A onto rod 214A. The operator may also pull sleeve 216A away from rod 214A to snap connectors 215A and 217A off rod 214A to completely detach sleeve 216A from rod 214A.

As also shown in FIG. 6, sleeve 216A includes a notch 600. A letter "S" is printed on sleeve 216A beneath notch 600, providing a visual indication to the operator that sleeve 216A is configured to hold a syringe containing saline. By looking at the letters printed beneath notch 600 on sleeve 216A and beneath notch 500 on sleeve 216B, the operator is able to correctly identify which sleeve is to hold a syringe containing contrast media, and which sleeve is to hold a syringe containing saline. In certain embodiments, device 200 is configured such that one sleeve is supposed to contain one type of medical fluid, while the other sleeve is supposes to contain a different type of medical fluid. Therefore, in these embodiments, it is important that the operator load a syringe having the correct type of fluid within sleeve 216A or 216B. By viewing the letter indicator "C" printed beneath notch 500, the operator is able to quickly identify sleeve 216B as the sleeve that is supposed to contain a syringe of contrast media. Likewise, by viewing the letter indicator "S" printed beneath notch 600, the operator is able to quickly identify sleeve 216A as the sleeve that is supposed to contain a syringe of saline (which is a diluent).

Notch 500 or 600 may also mate with tab 320 of syringe 301, in some embodiments. In these embodiments, the shape of notch 500 or 600 may be substantially similar to the shape of tab 320. Thus, for usability and ease of use, an operator may use such a mating mechanism to quickly and easily insert syringe 301 into sleeve 216A or 216B using the proper orientation of syringe 301 with the corresponding sleeve. Such an orientation may more easily allow, for example, the operator to properly connect tubing to ports 300 and 302 of syringe 301. The operator may align tab 320 of syringe 301 with either notch 500 or 600 when loading syringe 301 into the corresponding sleeve.

In addition, the provided mating mechanism may also serve as a means of protection against the operator inadvertently trying to insert the wrong type of syringe with a sleeve, according to one embodiment. In certain embodiments, the tab of a syringe containing contrast media may have a substantially different shape and/or size than the tab of a syringe containing saline. Similarly, in these embodiments, notch 500 of sleeve 216B may have a substantially different predefined shape and/or size than those of notch 600 in sleeve 216A. Notch 500, for instance, may have a shape and size substantially similar to the tab of the syringe containing contrast media, while notch 600 may have a shape and size substantially similar to the tab of the syringe containing saline. Thus, in these embodiments, notch 500 will only properly mate with the tab of a contrast media syringe, but will not properly mate with the tab of a saline syringe. Likewise, notch 600 will only properly mate with the tab of a saline syringe, but will not properly mate with the tab of a contrast media syringe. These mechanisms may substantially prohibit or disallow the operator from inadvertently trying to load the wrong type of syringe into sleeves 216A and 216B.

Figure 7:
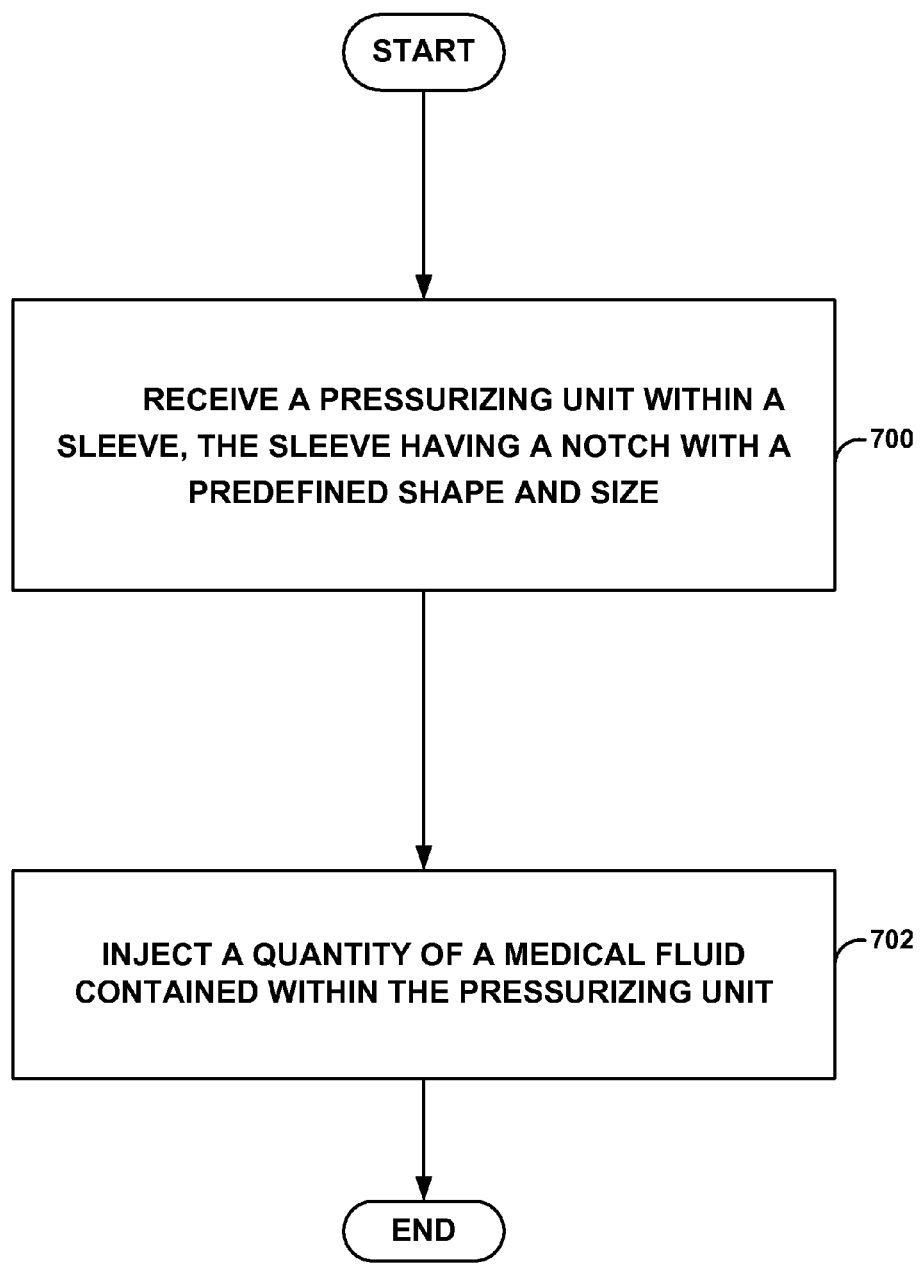
FIG. 7 is a flow diagram of a method that may be performed by a powered medical fluid injection device, according to one embodiment.

FIG. 7 is a flow diagram of a method that may be performed by a powered medical fluid injection device, according to one embodiment. For example, the method of FIG. 7 may be performed by device 100 (FIG. 1A) or device 200 (FIGS. 2A-2D). For purposes only of illustration, it will be assumed that device 200 performs the method shown in FIG. 7 in the description below.

In act 700, device 200 receives a pressurizing unit within a sleeve, such as sleeve 216A. Device 200 may include two such sleeves 216A and 216B. The pressurizing unit may comprise a syringe such as syringe 301 shown in FIGS. 3A-3C. The syringe that is inserted into the sleeve has an external tab with a predefined shape and size that are substantially identical to the predefined shape and size of the notch in the sleeve. In this way, the notch mates with the tab when the sleeve receives the pressurizing unit. Once the pressurizing unit has been inserted into the sleeve, device 200, in act 702, injects a quantity of medical fluid contained within the pressurizing unit.

Figure 8:
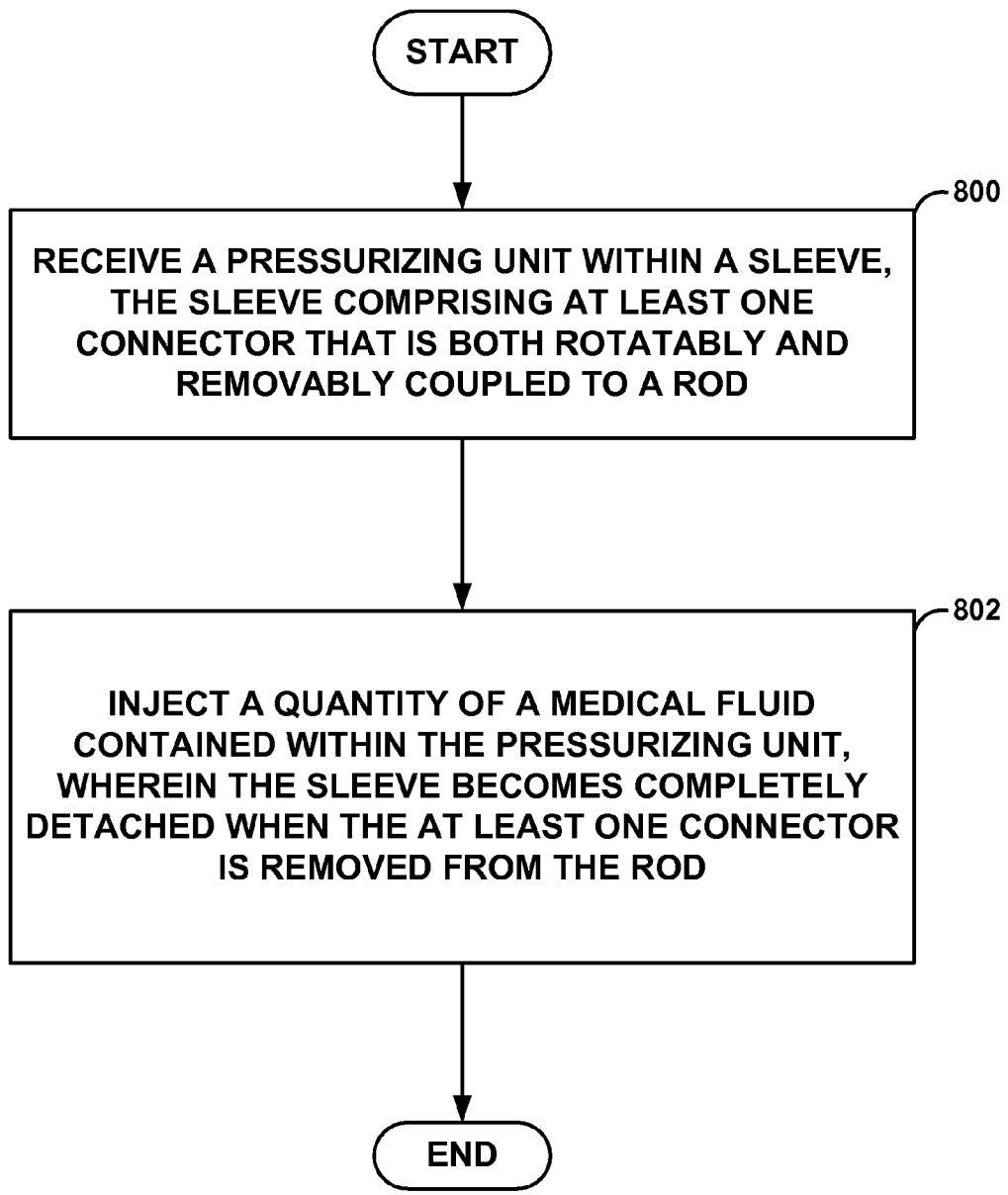
FIG. 8 is a flow diagram of another method that may be performed by a powered medical fluid injection device, according to one embodiment.

FIG. 8 is a flow diagram of another method that may be performed by a powered medical fluid injection device, according to one embodiment. For example, the method of FIG. 8 may be performed by device 100 (FIG. 1A) or device 200 (FIGS. 2A-2D). For purposes only of illustration, it will be assumed that device 200 performs the method shown in FIG. 8. In act 800, device 200 receives a pressurizing unit within one of its sleeves. For example, device 200 may receive syringe 301 within sleeve 216A. The sleeve includes at least one connector that is both rotatably and removably coupled to a rod of the device (such as, for example, rod 214A.) In act 802, device 200 injects a quantity a medical fluid contained within the pressurizing unit. Upon completion of the injection, the sleeve becomes completely detached from device 200 when the at least one connector is removed from the rod by an operator. For example, an operator may choose to completely detach the sleeve from device 200 in order to clean or replace the sleeve, as described previously.

Various embodiments have been described herein. These and other embodiments are within the scope of the following claims.

The invention claimed is:

1. A method comprising:
  receiving a pressurizing unit within a sleeve of a powered medical fluid injection device, such that the pressurizing unit is contained within the sleeve, wherein the sleeve has a notch with a predefined shape and size, and wherein the pressurizing unit has an external tab with a predefined shape and size that are substantially identical to the predefined shape and size of the notch in the sleeve, such that the notch mates with the tab when the sleeve receives the pressurizing unit;

receiving a second pressurizing unit within a second sleeve of the powered medical fluid injection device, such that the second pressurizing unit is contained within the second sleeve, wherein the second sleeve has a second notch with a predefined shape and size substantially different than the predefined shape and size of the notch of the sleeve, and wherein the second pressurizing unit has a second external tab with a predefined shape and size that are substantially identical to the predefined shape and size of the second notch of the second sleeve, such that the second notch of the second sleeve mates with the second external tab of the second pressurizing unit when the second sleeve receives the second pressurizing unit, wherein the predefined shape and size of the notch of the sleeve are substantially different from the predefined shape and size of the second external tab of the second pressurizing unit, such that the predefined shape and size of the notch of the sleeve prohibits the second pressurizing unit from being received within the sleeve, and wherein the predefined shape and size of the second notch of the second sleeve are substantially different from the predefined shape and size of the external tab of the pressurizing unit, such that the predefined shape and size of the second notch of the second sleeve prohibits the pressurizing unit from being received within the second sleeve; and injecting a quantity of a medical fluid contained within the pressurizing unit or the second pressurizing unit using the injection device.

2. The method of claim 1, wherein the mating of the notch of the sleeve and the tab of the pressurizing unit provides a proper alignment of the pressurizing unit within the sleeve.

3. The method of claim 1, wherein the predefined shape of the notch of the sleeve comprises a rectangular shape in cross section, and wherein the predefined shape of the tab of the pressurizing unit comprises a substantially identical rectangular shape in cross section.

4. A powered medical fluid injection device, comprising:
a sleeve having a notch with a predefined shape and size, wherein the sleeve is configured to receive a pressurizing unit that is inserted into the sleeve such that the pressurizing unit is contained within the sleeve, the pressurizing unit having an external tab with a predefined shape and size that are substantially identical to the predefined shape and size of the notch of the sleeve, such that the notch of the sleeve mates with the external tab of the pressurizing unit when the sleeve receives the pressurizing unit;
a second sleeve having a second notch with a predefined shape and size substantially different than the predefined shape and size of the notch of the sleeve, wherein the second sleeve is configured to receive a second pressurizing unit that is inserted into the second sleeve such that the second pressurizing unit is contained within the second sleeve, the second pressurizing unit having a second external tab with a predefined shape and size that are substantially identical to the predefined shape and size of the second notch of the second sleeve, such that the second notch of the second sleeve mates with the second external tab of the second pressurizing unit when the second sleeve receives the second pressurizing unit; and
an injector head coupled to the sleeve and to the second sleeve, wherein the predefined shape and size of the notch of the sleeve are substantially different from the predefined shape and size of the second external tab of the second pressurizing unit, such that the predefined shape and size of the notch of the sleeve prohibits the second pressurizing unit from being received within the sleeve, wherein the predefined shape and size of the second notch of the second sleeve are substantially different from the predefined shape and size of the external tab of the pressurizing unit, such that the predefined shape and size of the second notch of the second sleeve prohibits the pressurizing unit from being received within the second sleeve, and wherein the injector head is configured to inject a quantity of a medical fluid contained within the pressurizing unit during operation.

5. The medical fluid injection device of claim 4, wherein the mating of the notch of the sleeve and the tab of the pressurizing unit provides a proper alignment of the pressurizing unit within the sleeve.

6. The medical fluid injection device of claim 4, wherein the pressurizing unit comprises a syringe, and wherein the medical fluid comprises at least one of a contrast media and a diluent.

7. The medical fluid injection device of claim 4, wherein the predefined shape of the notch of the sleeve comprises a rectangular shape in cross section, and wherein the predefined shape of the tab of the pressurizing unit comprises a substantially identical rectangular shape in cross section.

8. The medical fluid injection device of claim 4, wherein the sleeve further includes a handle and at least one connector, wherein the handle is configured to be manipulated by an operator to load the sleeve into or unload the sleeve out of the injection device, and wherein the at least one connector is configured to couple the sleeve to a rod of the injection device.

9. The medical fluid injection device of claim 8, wherein manipulation of the handle by the operator causes the sleeve to rotate about the rod.

10. The medical fluid injection device of claim 4, wherein the sleeve further includes a visual indicator adjacent to the notch of the sleeve that specifies a type of pressurizing unit to be inserted into the sleeve.

11. The medical fluid injection device of claim 4, wherein the sleeve is rotatable around a rod of the medical fluid injection device into different operating positions, including a loaded and an unloaded position, without detaching the sleeve from the rod.

* * * * *